(12) United States Patent
Jonsson et al.

(10) Patent No.: US 7,306,912 B2
(45) Date of Patent: Dec. 11, 2007

(54) METHOD FOR TWO-DIMENSIONAL CONFORMATION-DEPENDENT SEPARATION OF NON-CIRCULAR NUCLEIC ACIDS

(75) Inventors: Jon Johannes Jonsson, Reykjavik (IS); Hans Guttormur Thormar, Reykjavik (IS); Gudmundur H. Gunnarsson, Reykjavik (IS); Bjarki Gudmundsson, Reykjavik (IS)

(73) Assignee: Lifeind EHF., Reykjavik (IS)

( * ) Notice: Subject to any disclaimer, the term of this patent is extended or adjusted under 35 U.S.C. 154(b) by 275 days.

(21) Appl. No.: 10/505,585

(22) PCT Filed: Feb. 25, 2003

(86) PCT No.: PCT/IS03/00011

§ 371 (c)(1),
(2), (4) Date: Aug. 25, 2004

(87) PCT Pub. No.: WO03/070943

PCT Pub. Date: Aug. 28, 2003

(65) Prior Publication Data

US 2006/0057575 A1    Mar. 16, 2006

Related U.S. Application Data

(60) Provisional application No. 60/360,107, filed on Feb. 28, 2002.

(30) Foreign Application Priority Data

Feb. 25, 2002  (IS)  .......................................... 6281

(51) Int. Cl.
*C12Q 1/68* (2006.01)
(52) U.S. Cl. ........................................................ 435/6
(58) Field of Classification Search .................... None
See application file for complete search history.

(56) References Cited

U.S. PATENT DOCUMENTS 5,874,212 A    2/1999  Prockop et al. ................. 435/6

FOREIGN PATENT DOCUMENTS

WO    WO-92-13101    *  8/1992
WO    WO-95/11993 A    5/1995
WO    WO-97/39149 A    10/1997

OTHER PUBLICATIONS

Uitterlinden et al, Proc. Natl. Acad. Sci. USA. 86: 2742 (1989).*
Woolley et al, Cancer chemother. pharmacol. 44(6), 511 (1999), abstract only.*
Hansen et al, Nucleic Acids Res. 24(5), 859 (1996), abstract only.*
Tang et al, Bulletin Chem. Soc. Japan 71(7), 1725 (1998), abstract only.*
Gao et al, Biochemistry 32: 9639 (1993), abstract only.*
Kovar, H. et al., "Two Dimensional Single-Strand Conformation Polymorphism Analysis: A Useful Tool for the Detection of Mutations in Long DNA Fragments", Nucleic Acids Research. England. vol. 19, No. 13.
Thomar et al., "From Genomic to Representational Mismatch Scanning", American Journal of Human Genetics, vol. 71, No. 4. p. 398. Oct. 2002.
Gunnarsson, G.H. et al., "2-D Conformation-Dependent Electrophoresis for Analysis of Complex DNA Samples (2D-CDE)." ###American Journal of Human Genetics, vol. 71, No. 4, p. 400. Oct. 2002.

* cited by examiner

*Primary Examiner*—James Martinell
(74) *Attorney, Agent, or Firm*—Birch, Stewart, Kolasch & Birch, LLP

(57) ABSTRACT

Methods are provided for separating linear nucleic acid fragments based on their conformation. The methods are based on novel two-dimensional gel electrophoresis techniques. In one aspect the method comprises electrophoresing a sample of nucleic acids in a first dimension said sample through a gel matrix under a first set of pre-determined electrophoresis conditions; electrophoresing said gel matrix in a second dimension under a second set of electrophoresis conditions, such that linear nucleic acid fragments of equal length but having different conformation are separated; said first and second electrophoresis conditions are different, such that in one of said dimensions electrophoresis allows separation of linear nucleic acid fragments based on conformation and length, and in the other of said dimensions electrophoresis allows separation of the sample fragments based substantially on length. Said difference is preferably established with a chemical agent capable of reducing conformational differences between linear nucleic acids fragments.

29 Claims, 14 Drawing Sheets

METHOD FOR TWO-DIMENSIONAL CONFORMATION-DEPENDENT SEPARATION OF NON-CIRCULAR NUCLEIC ACIDS

FIELD OF THE INVENTION

The present invention is in the field of nucleic acid analysis, specifically for screening nucleic acid preparations to identify, isolate, and characterize linear nucleic acid fragments with altered conformation. Examples include, but are not limited to, conformational alterations due to DNA polymorphism and modifications in structure of bases or backbone. Methods of the invention are especially useful for separation and isolation of non-circular mismatched DNA fragments from a complex mixture of hetero- and homohybrids based on their differences on conformation.

BACKGROUND OF THE INVENTION

Unusual secondary structures in linear DNA fragments often lead to significant conformational changes of the entire molecule. Such conformational changes of linear nucleic acids fragments frequently result in curvature, characterized by decreased end-to-end distance. Curvature has for example been detected or proposed in linear DNA fragments containing mispaired bases, insertion/deletion loops, UV-lesions, base adducts, base methylation, A-tracts, GGCC sequences, cross-links, DNA hairpins or cruciforms, slipped-strand structures, protein binding and nicking. DNA conformation in general, and conformational changes of linear DNA fragments because of altered secondary structure, have been analyzed using various direct and indirect methods such as X-ray diffraction, nucleic magnetic resonance spectroscopy (NMR), electron microscopy (EM), fluorescence resonance energy transfer (FRET), and gel retardation analysis.

Some gel electrophoresis methods allow separation of linear DNA fragments based on both length and conformation, while others separate DNA fragments based essentially on their length. Polyacrylamide gel electrophoresis (PAGE) is an example of a method in the former category and agarose electrophoresis an example of the latter. A rigorous physical theory of gel electrophoresis through a matrix capable of separating DNA fragments based on length, or both length and conformation, has not been presented. However, it has been recognized that PAGE allows conformation-dependent separation of linear DNA fragments in such way that migration decreases as the square of the degree of curvature for each linear DNA fragment separated [1]. This quantitative relationship between curvature and migration of linear DNA fragments has been used experimentally to evaluate DNA curving. Such methods are based on the fact that linear DNA fragments with altered conformation migrate at a different rate through a gel matrix compared to DNA fragments with normal conformation. These differences in migration rates can further be used to separate and isolate linear DNA fragments based on their conformation if the length of each fragment is known. In principle, it should be possible to separate linear DNA fragments of equal length with various conformations using PAGE with sufficient resolution.

A few previously described analytical methods used to screen for mutations or polymorphism are based on this principle. Heteroduplex analysis (HA) is a method used to scan for polymorphism by comparing migration rates of mismatched heterohybrids and perfectly matched hetero- and homohybrids. After melting and reannealing of homologous DNA samples from two or more individuals, the DNA mixture will contain both heterohybrids, some or all are mismatched if there is polymorphism between individuals, and perfectly matched homohybrids. Alternatively, the mixture will contain perfectly matched hetero- and homohybrids if the DNA samples are identical in sequence. After reannealing, the DNA mixture is analyzed using PAGE. If the sample contains mismatched heterohybrids, their migration will be retarded through the gel due to their altered conformation compared to the perfectly matched duplexes. Several variations to increase the sensitivity and reliability of HA have been developed. Conformation Sensitive Gel Electrophoresis (CSGE) is a well-known variation of HA [2, 3]. This system uses mildly denaturing solvents to enhance the tendency of single-base mismatches to produce conformational changes (see U.S. Pat. No. 5,874,212 to Prockop, et al.).

Use of previously described methods for conformation-dependent separation of linear DNA fragments, such as HA and CSGE, are limited to situations were the analyzed DNA molecules are of known length. In addition, only simple DNA samples containing one or at most a few different DNA fragments can be tested. If the sample contains a complex mixture of DNA fragments of different lengths it would be impossible to identify which of them show difference in migration because of their conformation since individual bands would overlap or not resolve sufficiently. This is a major drawback since it limits application of this technology. Similar limitations would also apply to other comparable techniques based on capillary electrophoresis or chromatography (e.g. dHPLC).

Methods for separating individual linear DNA fragments from a complex mixture based only on their difference in conformation, independent of their length, would be of great interest. Such methods would allow analysis of complex samples containing many linear DNA fragments of different length. Examples where such methods could be used include but are not limited to: Physical separation of mismatched heterohybrids and perfectly matched hetero- and homohybrids allowing isolation and enrichment of either class; simultaneous mismatch scanning of multiple fragments; isolation of damaged DNA molecules from bulk amount of undamaged molecules, and estimation of the efficiency of nucleic acid reannealing.

One possible way to achieve length independent, or essentially length independent, separation of linear DNA fragments based on their conformation is to develop two-dimensional (2-D) gel electrophoresis systems. Such a system would separate DNA fragments based on both length and conformation in one dimension but only on length in the other dimension.

Two different 2-D gel electrophoresis methods capable of separating linear DNA fragments based on conformation were described in the late eighties [4, 5]. These two methods use different approaches to resolve linear DNA fragments with certain conformations. Both of these methods provided separation of curved linear DNA fragments containing adenine-tracts (A-tracts). One of these methods combines agarose and PAGE electrophoresis using the different migration behavior of curved linear DNA fragments in these two matrixes. The other method uses temperature-dependency of DNA structure and conformation. By using different temperature for each dimension (10° C. and 60° C.) different conformations are induced resulting in differences in migration rates. DNA curvature due to A-tracts results from different stacking interactions between adjacent adenine bases in the molecule. A-tract curvature is not very rigid and can therefore be removed or reduced by increasing the temperature of the system [6, 7]. It is not disclosed or suggested in the prior art, that these or other systems can separate other more rigid conformations, such as those formed in mismatched or UV damaged duplexes. In our experience, it is not possible to separate mismatched duplexes from perfectly matched duplexes using temperature as a variable between the two dimensions. This is perhaps due to secondary and tertiary structures resulting from mismatches are less temperature dependent than in the case of A-tracts. The combined agarose-PAGE system is limited by difficulties in transferring linear DNA fragments between the two different matrixes in an efficient and reproducible manner.

A 2-D gel electrophoresis system using neutral-neutral agarose gel electrophoresis for the separation of relaxed circular DNA and supercoiled DNA from linear DNA using ethidum bromide in the second dimension is disclosed in WO 97/39149. In the first dimension, DNA molecules are separated in proportion to their mass using low voltage in low percentage agarose. The second dimension is run at high voltage in a gel of higher agarose concentration in the presence of the intercalator ethidium bromide. Under these conditions, mobility of all circular DNA molecules is drastically influenced by their shape but mobility of linear DNA fragments are essentially the same as in the first dimension. After separation and nucleic acid staining a pattern is detected. The pattern consist of generally three arcs lying in front of the forth arc which contains linear or linearized DNA. Arc 1 contains opened circles (relaxed) DNA. Arc 2 contains covalently closed circles that were converted to a relaxed form. Arc 3 contains covalently-closed (supercoiled) DNA. It should be emphasized that this method cannot be used to separate linear DNA fragments according to conformation because of the fact that linear DNA fragment of same length with different conformation are separated almost entirely according their size in agarose gel electrophoresis. Further, perhaps due to these limitations, the reference does not disclose or suggest 2-D gel electrophoresis methods for separating other types of conformational different DNA molecules, such as curved linear DNA fragments containing unusual secondary structure, e.g. mismatched duplexes.

Two types of 2-D gel electrophoresis system have been described for mapping origins of replication [8, 9]. One of the systems uses neutral-neutral agarose gel electrophoresis as described above. The other system uses neutral-alkaline agarose gel electrophoresis to achieve separation according to size and structure in the first dimension and only size in the second dimension. These systems allow separation of large non-circular DNA molecules with unusual structure such as those formed in replicons (large DNA bubbles and Y shaped DNA replication forks). Linear DNA fragments that are curved due to existence of local unusual secondary structure such as UV-lesion or insertion bulges cannot be separated in these systems. The difference in conformation of such linear DNA fragment with or without unusual local secondary structures is not great enough to ensure different migration in agarose elctrophoresis and will therefore not be detected in this system.

An ideal 2-D gel electrophoresis system for conformation-dependent separation of linear nucleic acids fragments would preferably be based on a single gel matrix eliminating the troublesome transfer step between two different gel matrixes. Such transfer often gives rise to trailing effects, which lower the detection capability of the system. A physical or chemical factor would then be introduced (or removed) after the first dimension to affect the conformation of different linear DNA fragments to a different degree depending on secondary and tertiary structure. Such physical or chemical factor should allow the differentiation of minor as well as major conformational differences, such as e.g. caused by single base pair mismatched DNA and insertion or deletion bulges.

Many chemical factors have been reported to affect conformation of linear DNA molecules, e.g. mono- and divalent cations such as $Na^+$ and $Mg^{2+}$. DNA curvature generally increases with increasing concentration of cations. Chemical factors that decrease curvature of DNA fragments containing unusual secondary structures would generally be of more interest than those that increase DNA curvature. Intercalators are small planar molecules, which form hydrophobic interactions with nucleic acids by insertion (intercalation) between DNA base pairs. Such interactions require untwisting of the DNA molecule to enable enough space between adjacent base pairs for the intercalator molecule. This separation of base pairs and concurrent untwisting results in increased length and stiffness of the DNA molecule thus affecting its whole conformation [10]. It has been reported that addition of intercalators to linear DNA fragments, curved because of A-tract, can greatly reduce the curvature [11-14]. This has been determined both with PAGE electrophoresis and electron microscopy studies. We have now defined conditions were some intercalators also greatly reduce the curvature of linear DNA fragments containing insertion/deletion loops or UV adducts as determined by gel retardation analysis in PAGE electrophoresis.

It is a well-known fact that linear single-stranded DNA fragments migrate essentially only according to length in PAGE containing highly concentrated denaturating chemical agents. Such behavior of single-stranded DNA is the basis of common techniques in DNA sequencing. We have found that after separation of mismatched DNA molecules both according to length and conformation it is possible to denaturate DNA molecules in the gel with addition of denaturating chemical agents and heating for given amount of time. Thus, it is possible to separate single stranded DNA fragments in the second dimension only according to length allowing formation of electrophoresis system capable of conformation dependent separation.

SUMMARY OF INVENTION

Methods are provided for, conformation-dependent separation of complex mixture of linear nucleic acid fragments independent of their length. Methods of the present invention can be applied to linear nucleic acid fragments obtained from different sources and they do not require any special prior manipulation of the nucleic acid fragments. The present invention provides general methods that can be used in different contexts such as but not limited to; physical separation of mismatched heterohybrids from perfectly matched hetero- and homohybrids allowing isolation and enrichment of either class; simultaneous scanning of multiple fragments for mutations; isolation of damaged DNA molecules from undamaged molecules; and estimation of efficiency of nucleic acid reannealing.

The method of the invention utilizes novel 2-D gel electrophoresis systems. Two general approaches of the method have been developed to achieve conformation-dependent separation in the system. Both approaches are based on linear DNA fragments being separated in the first dimension in a gel matrix where migration rate is determined according to both length and conformation. In this first dimension linear DNA fragments of equal length migrate at different rates if their conformation is different. After first dimension separation of linear DNA fragments the gel matrix is soaked in an electrophoresis buffer containing a chemical agent. In one approach the chemical agent reduces the differences in conformation between linear DNA fragments by reversible interaction. In the other approach, differences in conformation between linear DNA fragments are eliminated by converting DNA to a single stranded form. This is achieved by e.g. addition of a denaturing chemical agent and by keeping temperature above melting point for a given amount of time. In both approaches, the second dimension is then run preferably perpendicular to the first dimension. Running the second dimension at 90° to the first dimension offers greatest resolution although other angles could be used. In the second dimension, linear DNA fragments are separated essentially according to their length because differences in conformation have been minimized or eliminated.

The result of such 2-D gel electrophoresis methods is separation of all linear DNA fragments based on both differences in length and conformation. Migration of linear DNA fragments with normal conformation (lacking unusual local secondary structures) is primarily determined by their relative lengths in both dimensions resulting in a line or an arc of DNA fragments (in case of complex DNA samples) lying essentially diagonally through the gel matrix. Linear DNA fragments with altered conformation (e.g. due to mismatches or damage) migrate relatively at slower rate in the first dimension compared to the second dimension. Therefore, they are displaced in front of the arc of DNA fragments with normal conformation after the second dimension electrophoresis.

In alternative configurations of the method, agents are used that either increase or reduce the migration rates of linear DNA fragments with unusual conformation and they can be applied in either the first or second dimension. This could result in such DNA fragment with altered conformation being placed either behind or in front of the arc after the 2-D electrophoresis is completed. In general, however, having the DNA fragments of interest (typically those with unusual conformation) migrating in front of the arc is preferable. Using such an approach isolated preparations are purer since they are not contaminated with DNA fragments retarded from the arc due to trailing effects.

BRIEF DESCRIPTION OF THE FIGURES

FIG. 5a shows single-dimension separation of DNA fragments according to both conformation and length. FIGS. 5b-d show second dimension separation of two DNA fragments labeled 1 and 2. DNA fragment labeled 1 contains 3 cytosine bulge and it a positive control in the experiment. DNA fragment labeled 2 is a 281 bp restriction fragment from the replicative form of the plasmid phi-x digested with HaeIII. This DNA fragment contains A-tract and shows anomalous migration in polyacrylamide gel electrophoresis. DNA fragments labeled 3C-bulge and A-tract migrate relatively faster than other DNA fragments in the second dimension therefore allowing separation of DNA fragments containing two different unusual secondary structures from bulk of perfectly matched linear DNA fragments with normal secondary structure. The separation improved with increased electrophoresis time.

FIG. 10 shows second dimension conformational separation of two DNA fragments labeled 1 and 2. DNA fragment labeled 1 contains 3 cytosine bulge and DNA fragment labeled 2 is a 281 bp restriction fragment from the replicative form of the plasmid phi-x digested with Hae III. This DNA fragment contains A-tract and shows anomalous migration in polyacrylamide gel electrophoresis. DNA fragments labeled 1 and 2 migrate relatively faster than other DNA fragments in the second dimension therefore allowing separation of DNA fragments containing two different unusual secondary structures from bulk of perfectly matched linear DNA fragments with normal secondary structure using PAGE in first dimension and agarose electrophoresis in the second dimension.

FIGS. 11a and b shows genotyping of sequences isolated from the gel area in front of the arc. As can be seen the sequences are polymorphic within and between individuals. FIGS. 11c and d shows genotyping of sequences isolated from the arc itself. As can be seen the sequences are not polymorphic.

FIG. 12a shows 2-D electrophoresis of untreated pool of DNA fragments obtained by specified PCR allowing selective amplification of fragments 3' flanking sequences of Alu repeats. DNA fragments obtained with PCR from the pBR322 were used as standards for perfectly matched DNA fragments of various lengths. The DNA pool clearly travels in similar manner to perfectly matched DNA fragments obtained from the plasmid resulting in formation of arc containing linear DNA fragments of a broad length range. In FIG. 12b a reannealed pool of DNA fragments is analyzed. This DNA pool shows a similar behavior as obtained for untreated pool (FIG. 12a) but the arc formed has a narrower length range. If the same DNA pool is denatured at 95° C. for 5 min, rapidly cooled on ice, then analyzed on 2-D gel, completely different behavior is obtained (FIG. 12c). As expected only minority of the DNA in pool form perfectly matched DNA fragments. Therefore only perfectly matched DNA fragments from the plasmid form the arc. Instead DNA fragments from the pool travel in front of the arc indicating unusual structures due to lack of complete reannealing. Pooled genomic DNA digested with Sau3AI was also analyzed with 2-D gel electrophoresis after the denaturation and attempt of reannealing. Because of great complexity of the human genome such reannealing is very inefficient. Indeed only perfectly matched PCR products from the plasmid form the arc (FIG. 12d).

DETAILED DESCRIPTION OF THE INVENTION

Figure 1:
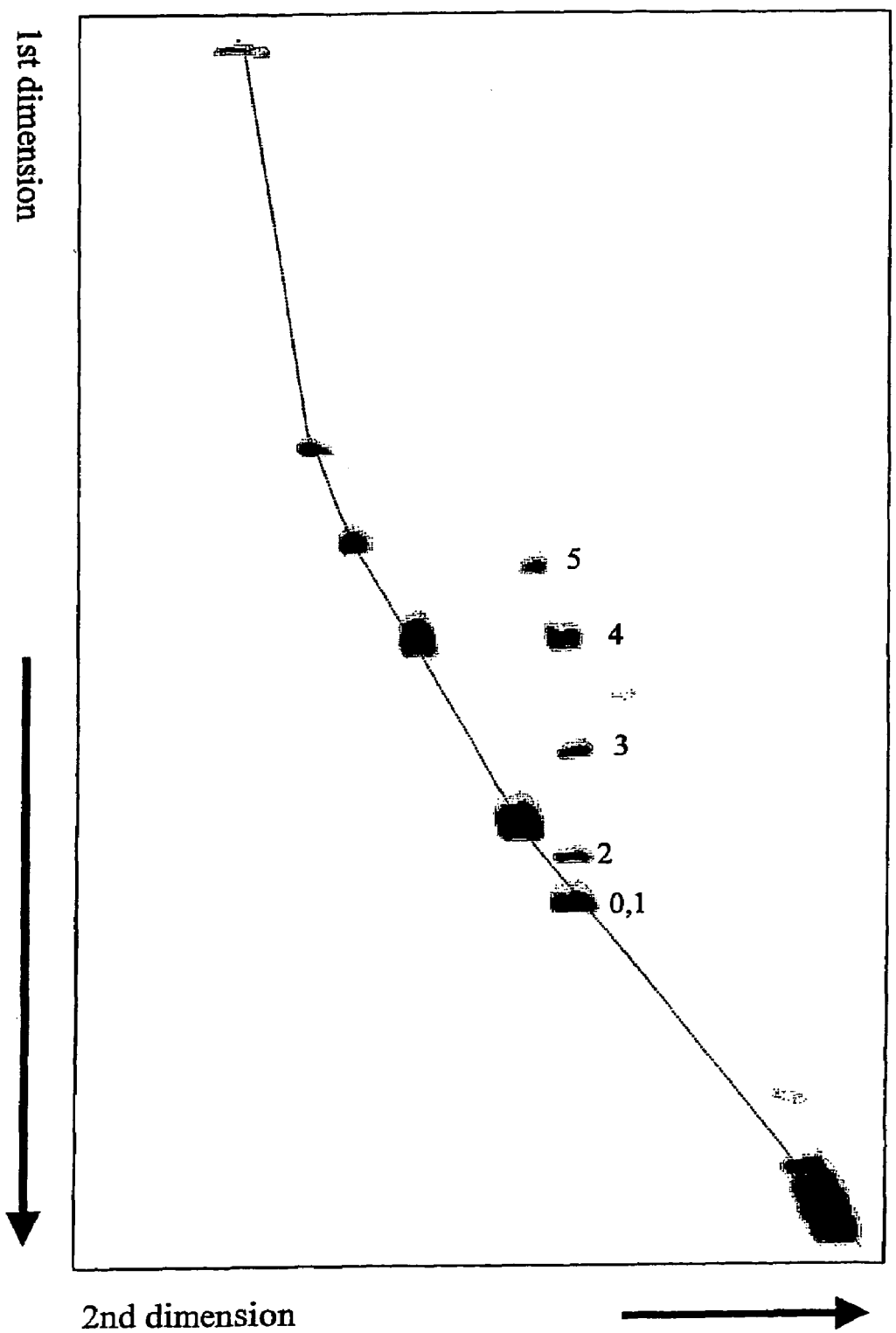
FIG. 1 is a fluorescent image of 2-D gel analysis conducted as described in Example 1. The gel shows formation of an arc containing perfectly matched linear DNA fragments and linear DNA fragments containing one cytosine bulge, which does not resolve in the this particular example. A dotted line is drawn between perfectly matched linear DNA fragments to further emphasize the arc. DNA spots labeled from 0 to 5 show the location of 298 bp linear DNA fragments containing cytosine bulges where the number of cytosine nucleotides in the bulge equal the label number. DNA fragments containing cytosine bulge in the size range between 2 and 5 nucleotides clearly migrate in front of the arc and therefore show a separation from perfectly matched DNA fragments in a mixture containing many fragments of different lengths. Although the bulge-containing DNA fragments which are of equal length, migrate at a similar rate in the second dimension the difference due to conformation is not completely eliminated. These fragments therefore form a slight arc. The fragment containing the largest bulge migrated at the slowest rate in first dimension and therefore it is has the largest displacement from the arc in the second dimension.

This invention provides a method for screening complex samples of nucleic acids fragments with or without prior knowledge of their biological function or genome location, to separate and optionally isolate nucleic acids based on differences in conformation. Linear DNA fragments with altered conformation can be produced from various different schemes including but not limited to:

a) Formation of mismatched linear DNA fragments by hybridization: Two samples or two pools of samples can be mixed together and denatured so all duplexes separate into single stranded fragments. The mixture can be cooled so single strands reanneal into a mixture of homo- and heterohybrids. Parameters, such as time and temperature for the melting of duplexes are known to those skilled in the art, as are the parameters necessary for rehybridization. Heterohybrids in this context are linear DNA fragments comprised of two nucleic acid strands from different sources. They can be either perfectly matched or mismatched. Perfectly matched heterohybrids In this context refers to linear double stranded nucleic acid containing perfectly complementary strands from two different sources. Formation of mismatched heterohybrids occurs where the strands from two different sources are only substantially complementary, but can contain regions of non-complementary strands, e.g. one or more mismatched base-pairs. Regions of non-complementary strands may cause loops to form within one or both strands of the mismatched heterohybrid. There may be as few as one region of non-complementary strands per mismatched heterohybrid, or more regions, so long as the heterohybrid can form under conditions selected for hybridization. A non-complementary region may include insertions or deletions of one or more bases of one strand relative to the other strand. Homohybrid in this context refers to linear double stranded nucleic acid containing perfectly complementary strands both from the same source (chromosome).

b) Modification of nucleic acids: Nucleic acids can be modified in such a manner that their conformation is altered. Such modifications can be part of intracellular mechanisms (e.g. methylation), spontaneous damage (e.g. deamination), or due to chemical compounds and physical agents that are present in the environment. One example of a physical agent that can cause changes in structure and conformation of nucleic acids is ultraviolet (UV) radiation. Exposure of DNA molecules to UV radiation can cause adjacent pyrimidine bases to be covalently modified given rise to photoproducts such as cyclobutan pyrimidine dimmer (CPD), pyrimidine-pyrimidone (6-4) and Dewar isomer. These three major photoproducts induce alteration in conformation of linear nucleic acids fragments containing such molecular lesions.

c) Intrinsic curvature of DNA: There are established cases of DNA existing in a permanently bent form without any external constraints. Such intrinsic curvature is a sequence-dependent property and it is conferred both by short runs of A or T nucleotides and by sequences such as GGCC repeated in phase with the helical repeat. Linear DNA fragments containing such sequences have different conformation compared to DNA fragments not containing them.

d) Tertiary structures: DNA can adopt alternative tertiary structure contrasting with the rather uniform structure of the classical B-form double helix, which shows little variation as a function of its nucleotide sequence. Many known tertiary large-scale nucleic acids structures can give rise to altered conformation of linear DNA fragments containing them. Examples include intramolecular triple stranded DNA, DNA and RNA cruciform structures and junctions, and slipped mispaired DNA.

e) Hydrolysis of one strand (nicking) or gapped structures: Linear DNA fragments can adopt altered conformation if they contain nicks or single base gaps. Generally gapped structures shows two families of conformation. One is close to the B-DNA the other is significantly kinked at the gap. Nicked DNA fragments show smaller differences in conformation compared to single base gap. Their conformational differences can be enhanced using 7M urea.

f) DNA-ligand interaction: It is well-know that ligands forming interaction to DNA fragment change greatly affect the conformation of the DNA. Protein interaction can significantly change the conformation of DNA. Perhaps the most prominent example of protein-induced DNA bending is the formation of chromatin. DNA bending also plays a crucial role in the regulation of gene expression. DNA binding proteins like IHF and transcriptions factors like CAP or TBP also introduce severe bends into the DNA. For example Integrated host factor (IHF) that is an architectural protein that bends double-stranded DNA by 160° at a specific recognition sequence.

As can be inferred from the description herein, the invention is particularly concerned with the analysis of linear, i.e. non-circular nucleic acids, that is, not e.g. supercoiled DNA or other compact tertiary structures of nucleic acids.

The nucleic acids samples suitable for analysis according to the present invention typically comprise linear fragments of a length in the range of 50 to 10000 bp, such as the range of 100 to 5000, but generally preferably in the range of 100-1000 bp. The source of nucleic acids fragments may be prokaryotic, eukaryotic, viral, or synthetic. The source may be genomic DNA, cDNA, RNA, DNA/RNA hybrids, LNA, PNA, plasmid DNA, or viral DNA or duplexes thereof, including where the virus may be naturally occurring or serving as a vector for nucleic acids from a different source, or the like. Depending upon the source of nucleic acids fragments, they may have to be subject to some purification, such as isolation from cellular source, separation from proteins, removal of restriction enzyme and PCR inhibitors, etc. It should be emphasized that the method is particularly advantageous as it can be applied to complex DNA samples, i.e. samples containing large numbers of different linear nucleic acid fragments, such as e.g. at least 100, or at least 500 or at least 1000 fragments; such as fragments of whole genomes or subsets thereof, and mixtures of genomic DNA from more than one individual. Complex samples cotain so many different fragments of different length that they do not resolve in one dimensional separation. This includes fragments migrated aberrantly due to altered conformation.

Linear nucleic acids fragments of desired length can be provided, particularly in case of DNA, by restriction enzyme digestion, use of PCR technology, ligation, chemical or physical induced cleavage and the like. Target nucleic acids may be labeled by isotopic or non-isotopic methods and they can contain a tag to allow specific capture after the separation. In some embodiments of the methods, adaptors or linkers are ligated to the nucleic acid fragments.

In a first aspect of the invention, a method is provided for separating non-circular nucleic acids fragments based on their conformation, comprising: providing a sample of linear nucleic acid fragments; loading the sample in a gel electrophoresis apparatus and electrophoresing in a first dimension said sample through a gel matrix under a first set of pre-determined electrophoresis conditions; electrophoresing said gel matrix in a second dimension under a second set of electrophoresis conditions, such that nucleic acids of equal length but having different conformation are separated, wherein said first and second electrophoresis conditions are different, such that in one of said dimensions electrophoresis allows separation of the sample nucleic acid fragments based on conformation and length, and in the other of said dimensions electrophoresis allows separation of the sample fragments based substantially on length, wherein said difference is established with chemical agent which is capable of reducing or increasing conformational differences between linear nucleic acids fragments.

In some embodiments of the method, first dimension gel electrophoresis is done under non-denaturating conditions using polyacrylamide gel or another gel matrix containing crosslinkers in accordance with methods of the present invention. Another embodiment of the methods utilizes mildly denaturating conditions to enhance conformational separation of DNA fragments in the first dimension. One objective for using this second approach would be separation of linear nucleic acid fragments containing single base pair mismatches. This can be achieved e.g. by addition of low concentration of urea or using Conformation Sensitive Gel Electrophoresis (CSGE) in the first dimension (see U.S. Pat. No. 5,874,212 to Prockop, et al).

Polyacrylamide gels useful in the methods of present invention may contain a wide percentage range of polyacrylamide according to the preferable length distribution of targeted linear nucleic acids fragments. Typically, they contain in the range of about 5% to about 15% polyacrylamide.

Size of the gel and electrical conditions can be adjusted according to the degree of migration necessary to maximize separation of nucleic acid fragments with different conformations.

Electrophoresis buffer systems for either of the dimensions can be chosen according to the gel matrix used in each specific embodiment of the method of invention. The same buffer system is not necessarily used in both dimensions.

Depending on the specific objective of the first dimension as discussed above, the first gel electrophoresis step can be carried out at widely different temperatures but in a typical application, the temperature is kept at a selected temperature between 5° to 50° C. In a typical embodiment of the method of the invention, mixtures of mismatched heterohybrids and perfectly matched hetero- and homohybrids are separated at 35° C. to ensure that curvature of linear DNA fragments containing A-tracts and CCGG repeats is limited. Such curvature is more pronounced at low temperature.

After first dimension electrophoresis, which allows both separation according to length and conformation of linear nucleic acid fragments as discussed above, the gel is preferably removed from the electrophoresis apparatus and soaked in buffer. The gel is soaked in the buffer for a period of time, which can vary depending on the size, matrix type and thickness of the gel used in the embodiment of the method. This buffer is typically made from the electrophoresis buffer used in the second dimension (for instance TBE) containing one or more chemical agent. The buffer allows reduction or elimination of the differences in conformation between linear nucleic acids fragments inside the gel matrix. Said chemical agent in the buffer is generally a molecule capable of forming interactions with nucleic acids, such as a natural or synthetic intercalating molecule, or a groove-binding molecule.

In certain embodiments of the method, the chemical agent may be a charged molecule capable of forming electrostatic interactions to nucleic acids.

It should also be noted that in addition to said chemical agent, the conditions in the second dimension electrophoresis can be different from those of the first dimension by altering a physical agent or parameter, such as temperature, which will further affect the conformation of the sample nucleic acids.

The buffer contains at least one chemical agent selected from the group consisting of but not limited to; natural or synthetic intercalators and bisintercalators such as ethidium bromide, aclacinomycin, chloroquine, distamycin-ellpticine, daunomycin, bleomycin, benzo[a]pyrene, iremycin, proflavin, cl-958, quiacrine, actionmycin, DEAP fluoranthene, psoralene, bisantrene, ditercalinium, BBM-938A, echinomycin, and TOTO; groove binding agents such as netropsin, distamycin, Hoechst 33258, and SN 6999; denaturating agents such as an aliphatic alcohol such as methyl, ethyl, isopropyl, n-propyl, allyl, butyl, isobutyl, and amyl alcohols and ethylene glycol; cyclic alcohols such as cyclohexyl, benzyl, phenol, and p-methoxyphenol alcohol and inositol; alicyclic compounds such as aniline, pyridine, purine, 1,4-dioxane, butyrolactone, and aminotriazole; amides such as formamide, ethylformamide, dimethylformamide, acetamide, N-ethylacetamide, N,N-dimethylacetamide, propionamide, glycolamide, thioacetamide, valerolactam; urea compounds such as carbohydrazide, 1,3-dimethylurea, ethylurea, t-butylurea, thiourea, and allylthiourea; carbamates such as urethan, N-methylurethan and N-propylurethan, detergents including Tween 40 and Triton X-100, and other compounds such as cyanoguanidine, sulfamide, glycine, and acetonitrile. Other chemical agents and physical factors that can be used in the present inventions to reduce differences in conformations may be identified or developed by those skilled in the art. The concentration of said chemical agent used in the method of invention is dependent on its nucleic acid binding affinity, ability to reduce conformational difference, and stability of the agent in the buffer.

After incubation for a suitable amount of time the gel is inserted in the second dimension electrophoresis apparatus. Interaction between the chemical agent/s and linear nucleic acid fragments results in reduced conformational difference between the nucleic acids fragments. Therefore linear nucleic acid fragments essentially, or exclusively, separate according to their length. By running the second dimension electrophoresis perpendicular to the first dimension it is possible to separate linear nucleic acid fragments that migrate only according to length (e.g. perfectly matched duplexes) from those that migrated both according to length and conformation in the first dimension (e.g. mismatched duplexes). This separation is dependent on the degree of reduction of conformational differences between nucleic acid fragments. After the second dimension electrophoresis all nucleic acids fragments of normal structure, i.e. perfectly matched without unusual curvature now form an arc or line positioned essentially diagonally through the gel. Linear nucleic acids fragments, where migration was affected by unusual conformation migrate relatively faster in the second dimension and they are therefore displaced in front of the arc. The result is separation of linear nucleic acid fragments based on conformation but independent of their length.

Nucleic acids fragments in the gel can be readily detected using standard biochemical techniques. They include well-known methods such as post-staining of the gel with fluorescent nucleic acid stains like ethidium bromide and SYBR® green I using detection systems familiar to those skilled in the art. In some embodiments of the method of invention the chemical agent used to reduce conformational difference between nucleic acids also serves as fluorescent nucleic acid stain eliminating the need for post-staining to visualize nucleic acids. Nucleic acids can also be detected using isotopic or non-isotopic pre-labeled nucleic acids and detection systems such as phosphor- and fluoroimagers or similar methods familiar to those skilled in the art.

Isolation of nucleic acid fragments from the gel after the 2-D gel electrophoresis may be done using well-known methods such as elution from gel pieces and electro-elution. Nucleic acid fragments may in some embodiments of the methods contain adaptors to ensure PCR amplification after the isolation from the gel matrix.

In a particularly useful embodiment of the method the intercalating molecule ethidium bromide is added to the second dimension electrophoresis buffer to reduce, before the second dimension electrophoresis, conformational differences between; a) mismatched and perfectly matched linear DNA fragments, b) linear DNA fragment curved due to existence of A-tract from uncurved DNA fragments, c) linear DNA fragments containing UV lesions and intact linear DNA fragments and d) linear DNA fragments containing nicked strand from intact linear DNA fragments.

In another embodiment of the method, the gel is soaked in electrophoresis buffer containing the denaturating agent urea after the first dimension. Then the temperature is raised in the gel matrix until all DNA fragments are single stranded allowing elimination of conformational differences between mismatched and perfectly matched linear DNA fragments before the second dimension.

One way of altering the conditions between the first and second dimension electrophoresis is to use a different gel matrix, e.g. polyacrylamide in one dimension and agarose in the other dimension. Consequently, in a related aspect of the invention a method is set forth for separating non-circular nucleic acid fragments based on their conformation, comprising the steps of: providing a sample of linear nucleic acid fragments; loading the sample in a gel electrophoresis apparatus and electrophoresing in a first dimension said sample through a gel matrix under a first set of predetermined electrophoresis conditions; electrophoresing said sample in a second dimension under a second set of electrophoresis conditions, such that linear nucleic acids fragments of equal length but having different conformation are separated; wherein said first and second electrophoresis conditions are different, such that in one of said dimensions electrophoresis is run in a agarose gel matrix and said conditions allowing separation of the sample nucleic acid fragments based substantially on their length, and in the other of said dimensions electrophoresis is run in an polyacrylamide matrix and said conditions allowing separation of the sample nucleic acid fragments based both on length and conformation, which method is capable of conformation-dependent separation of nucleic acids fragments having one or more features selected from: insertion/deletion loops, mismatched nucleic acids, slipped mispaired nucleic acids; base methylation; base damage, photoproducts resulting from UV damage, base damage by ionizing radiations, oxidative damage of bases, GGCC repeats, purine-pyrimidine tracts, addition of base adducts, triple stranded nucleic acids, cruciform structures, repetitive sequences, DNA Z-helix, protein bound nucleic acids, hairpin loops, AP sites, base gaps and nicks.

In one embodiment of the present invention a nucleic acid sample is incubated with a given protein, peptide or antibody prior to the 2-D gel electrophoresis. If any of the nucleic acid fragments contains a suitable binding substrate for the given protein, peptide or antibody a stable complex is formed. That complex would migrate at a slower rate in the first dimension gel electrophoresis both because of greater size of the complex and different conformation of the linear nucleic acid fragment. Before second dimension electrophoresis gel would be socked in buffer allowing destabilation of the complex by elimination of reversible interactions between components of the complex. Therefore second dimension migration of linear DNA fragments would be determined only by their length allowing separation of nucleic acid fragment bound to protein in the first dimension from those that did not form the interaction. This approach allows separation and subsequent isolation of nucleic acid sequences with binding sites for the tested protein, peptide or antibody.

The accompanying Examples (1 to 10) demonstrate the usefulness of such embodiments.

As described herein, the method of the present invention can be readily applied to separate linear DNA duplexes with unusual conformations due to many diffrent features from normal linear DNA duplexes, these features that can cause DNA to have an altered conformation which can be separated according to the invention can be one or more of the following: insertion/deletion loops, mismatched nucleic acids, slipped mispaired nucleic acids, base methylation, base damage, photoproducts resulting from UV damage, base damage by ionizing radiations, oxidative damage of bases, sequences resulting in intrinsic curvature such as adenine-tracts and GGCC repeat, purine-pyrimidine tracts, addition of base adducts, triple stranded nucleic acids, cruciform structures, repetitive sequences, DNA Z-helix, protein bound nucleic acids, hairpin loops and single-strand nicks.

In yet a further aspect of the invention, a method is provided for detection and isolation of polymorphic nucleic acids comprising a two-dimensional electrophoresis conformation-based separation as described above, wherein the nucleic acid sample comprises linear nucleic acid fragments from one individual or is pooled from a plurality of individuals, which nucleic acids have been digested, denatured and re-annealed, wherein the denaturing and re-annealing steps are done after mixing of the pooled samples, to provide a mixture of homo- and heterohybrids, wherein the method separates mismatched heterohybrids comprising polymorphic nucleic acids from mixture of perfectly matched homo- and heterohybrids.

The mismatched heterohybrids comprising polymorphic nucleic acids may then readily be isolated, e.g. as described above, to identify said nucleic acids fragments.

As is illustrated with a particular embodiment in Example 13 below, the method can be applied to a nucleic acid sample which is pool comprising a genome or genomic subsets from more than one individual. In a Useful embodiment of this kind, the sample to be analyzed comprises linear nucleic acid fragments that have been digested, denatured and re-annealed, wherein the denaturing and re-annealing steps are done before or after mixing of the samples or pooled samples, to provide a mixture of homo- and heterohybrids. In such applications, the subsample from each individual may be a subset of its genome (which is the case in Example 13) obtained with any of numerous methods well known to person skilled in the art. In useful embodiments, such a subset or pool of subsets is a highly polymorphic subset of said genomes.

Depending on desired objective of the invention for a given application the sample to be analyzed can be from a single individual, a plurality of individuals, a genomic subset from one individual or the same genomic subset from a plurality of individuals, or a combined pool of a number of pools, wherein the nucleic acids may be treated in various ways before or after pooling samples and/or combining pools, e.g. digested, denatured and reannealed.

In certain embodiments of the method of invention, genomic representations are used instead of genomic DNA. Methods for creating genomic representations have been described (e.g. PCT/US99/24984 to Yale University).

In some embodiments, isolated fragments with normal or unusual conformation are labeled with signals and hybridized to arrayed libraries, arrayed libraries of selected subsets of genomic clones or metaphase chromosomes.

Another related aspect of the invention provides a method for conformational separation of complex DNA sample from an individual or pools, where allele frequency differs between individuals or pools of individuals, comprising: forming DNA pool by mixing two or more DNA samples together or forming DNA sample from one individual, annealing specific adaptors to DNA fragments in the pool or DNA sample from one individual, removing excess adaptors that are not ligated to the DNA fragments, mixing two or more pools together, denaturing the mixture of pools of DNA samples or DNA sample from an individual, reannealing said pools of DNA samples to form DNA duplexes comprising homologous strands, and separating duplexes containing unusual conformation formed either by mismatched base pairs or insertion/deletion loops from perfectly matched DNA duplexes having normal conformation by the electrophoresis separation method as described above.

In a useful embodiment of the method of invention, reannealed DNA samples from an individual, two or more individuals or two or more groups of individuals are separately subjected to 2-D gel electrophoresis to isolate and characterize sequences associated with particular phenotype shown in an individual or a group of individuals. After isolation of either perfectly matched homo- and heterohybrids or mismatch homo- and heterohybrids, a comparative genome hybridization (CGH) of the isolated DNA fragments is carried out to detect differences in polymorphism within an individual genome or between two individuals or the two groups of individuals.

In one embodiment of the method, nucleic acid samples from one or more individuals are used as a "tester" against nucleic acid samples from one or more individuals serving as a "driver" in a subtractive hybridization, which is a method well-known to those skilled in the art. The method is used to isolate fragments that exist only or in higher concentration in one genomic sample or pool of samples than in the other sample(s). Subtractive hybridization can be done prior to gel analysis and gel isolation in order to but not limited to separating perfectly matched homo- and heterohybrids from mismatched. Subtractive hybridization can also be used after gel isolation for identifying differences between samples isolated from the gel. That includes samples with different adaptors for amplification from gel isolation.

In a further aspect of the invention, a method is provided for estimating efficiency of reannealing of a nucleic acid sample. In a typical embodiment of the method genomic samples or pool of samples that have been digested, denatured and reannealed are loaded on the gel. Before 2-D gel electrophoresis the genomic material is mixed with perfectly matched linear DNA fragments, which serve as a standard for migration of perfectly matched DNA in the system. The estimation of reannealing efficiency is based on the fraction of perfectly matched genomic material in the arc formed from by perfectly matched standards.

EXAMPLES

Example 1

Separation and Detection of Cy5 Labeled Linear DNA Fragments Containing Cytosine Bulges from Perfectly Matched Linear DNA Fragments Using Intercalator Approach.

Five diffrent 298 bp linear DNA fragments were prepared. Each fragment contained one defined cytosine bulge at its center with the bulge size ranging from 1 to 5 cytosines. Otherwise the DNA fragments were identical to each other. A perfectly matched 298 bp linear DNA fragment was also prepared. Execpt for not having a cytosine bulge this fragment had identical base sequence compared to the bulged DNA fragments. These 298 bp linear DNA fragments were prepared using three shorter DNA fragments. Two fragments were PCR amplified from the plasmid pBR322. One fragment (127 bp) was 5' end-labeled with Cy5 fluorescent molecule and contained 3' asymmetric overhang after digestion with Ava I. The other (132 bp) contained 5' asymmetric overhang after digestion with Ban II. One fragment (31 bp) was synthesized as two oligonucleotides to contain the specific cytosine bulge. It had 5' and 3' asymmetric overhangs each complementary to one of the overhangs on the other two fragments. Ligation of all three fragments in equimolar concentration resulted in the formation of one 298 bp DNA fragment containing the specified bulge at the center of the fragment.

Five perfectly matched linear DNA fragments (155 bp, 357 bp, 543 bp, 857 bp and 1395 bp), containing 5' Cy5 label, were also prepared using PCR amplification from the plasmid pBR322.

A mixture of all fragments described above was separated by 2D-CDE gel electrophoresis. The gel matrix consisted of 10% polyacrylamide prepared from 29:1 acrylamide:bisacrylamide mixture. The gel was polymerized in 1×TBE buffer (89 mM Tris base, 89 mM borate, and 2 mM EDTA) for 1 hour. The first dimension electrophoresis was done in Hoefer SE 660 vertical electrophoresis system using 18×24 cm glass sandwich with 1 mm spacers. The gel was run at 35° C. for 2 hours at 10 W with 1×TBE in both upper and lower buffer chambers. The gel was removed from the glass sandwich and soaked in 100 ml of 1×TBE buffer containing 5 micrograms/ml ethidium bromide. The gel was incubated for 10 min in the buffer and then washed briefly in 100 ml of 1×TBE buffer.

Second dimension gel electrophoresis was carried out in a Pharmacia Multiphor horizontal electrophoresis system. The gel was run at 20° C. for 2 hours at 10 W perpendicular to the first dimension electrophoresis using 1×TBE buffer containing 5 microgram/ml ethidium bromide in both buffer chambers. Connection between electrodes in buffer chambers to gel matrix was achieved with paper electrode wicks. After the second dimension gel electrophoresis the gel matrix was washed in 200 ml of 1×TBE for 5 minutes.

Fluorescent detection of linear DNA fragments was carried out using fluorescence-scanning mode of the AP Biotech's Typhoon 8600 variable mode imager using excitation wavelength 633 nm and the 670BP30 emission filter for the scan. As shown in FIG. 1, all perfectly matched DNA fragments form an arc lying diagonal through the gel. DNA fragments containing 2 to 5 cytosine bulges clearly travel in front of the arc but the 1 cytosine bulge is not resolved in this particular gel matrix from its perfectly matched DNA counterpart.

Example 2

Separation and Detection of Linear DNA Fragments Containing Cytosine Bulges at their Center or Near One End of the Fragment from Perfectly Matched DNA Fragments Using Intercalator Approach.

Unlabeled linear DNA fragments containing defined cytosine bulges were prepared as described in Example 1. Instead of doing equimolar ligation, ligation with excess of one end fragment was done resulting in formation of two major ligation products. One was the 298 bp product with the bulge at the center as described in Example 1. The other was a 158 bp product formed by ligation between the 31 bp synthetic molecule containing the bulge molecule and the 127 bp PCR fragment. This fragment has the bulge 15 bp from its end.

Five perfectly matched DNA fragments (155 bp, 357 bp, 543 bp, 857 bp and 1395 bp) containing 5' Cy5 label were also prepared using PCR amplification from the plasmid pBR322.

A mixture of the fragments described above was separated by 2-D CDE gel electrophoresis. The gel matrix consisted of 10% polyacrylamide prepared from 99:1 acrylamide:bisacryloylpiperazine (BAP) mixture. The gel was polymerized in 1×TTE buffer (90 mM Tris HCl, 30 mM taurine and 1 mM EDTA at pH 9.0). The first dimension electrophoresis was done in a Hoefer SE 660 vertical electrophoresis system using 18×24 cm glass sandwich with 1 mm spacers. The gel was run at 35° C. for 2 hours at 10 W with 1×TTE in both upper and lower buffer chambers. The gel was removed from the glass sandwich and soaked in 100 ml of 1×TTE buffer containing 5 micrograms/ml of ethidium bromide. The gel was incubated for 10 min in the buffer and then washed briefly in 100 ml of 1×TTE buffer.

Second dimension gel electrophoresis was done in a Pharmacia Multiphor horizontal electrophoresis system. The gel was run at 20° C. for 2 hours at 10 W perpendicular to the first dimension electrophoresis using 1×TTE buffer containing 5 microgram/ml ethidium bromide in both buffer chambers. Connection between electrodes in buffer chambers trough gel matrix was achieved with paper electrode wicks. After the second dimension gel electrophoresis the gel matrix was placed in UVP GDS-8000 gel documentation system for UV detection of ethidium bromide stained DNA fragments.

Figure 2:
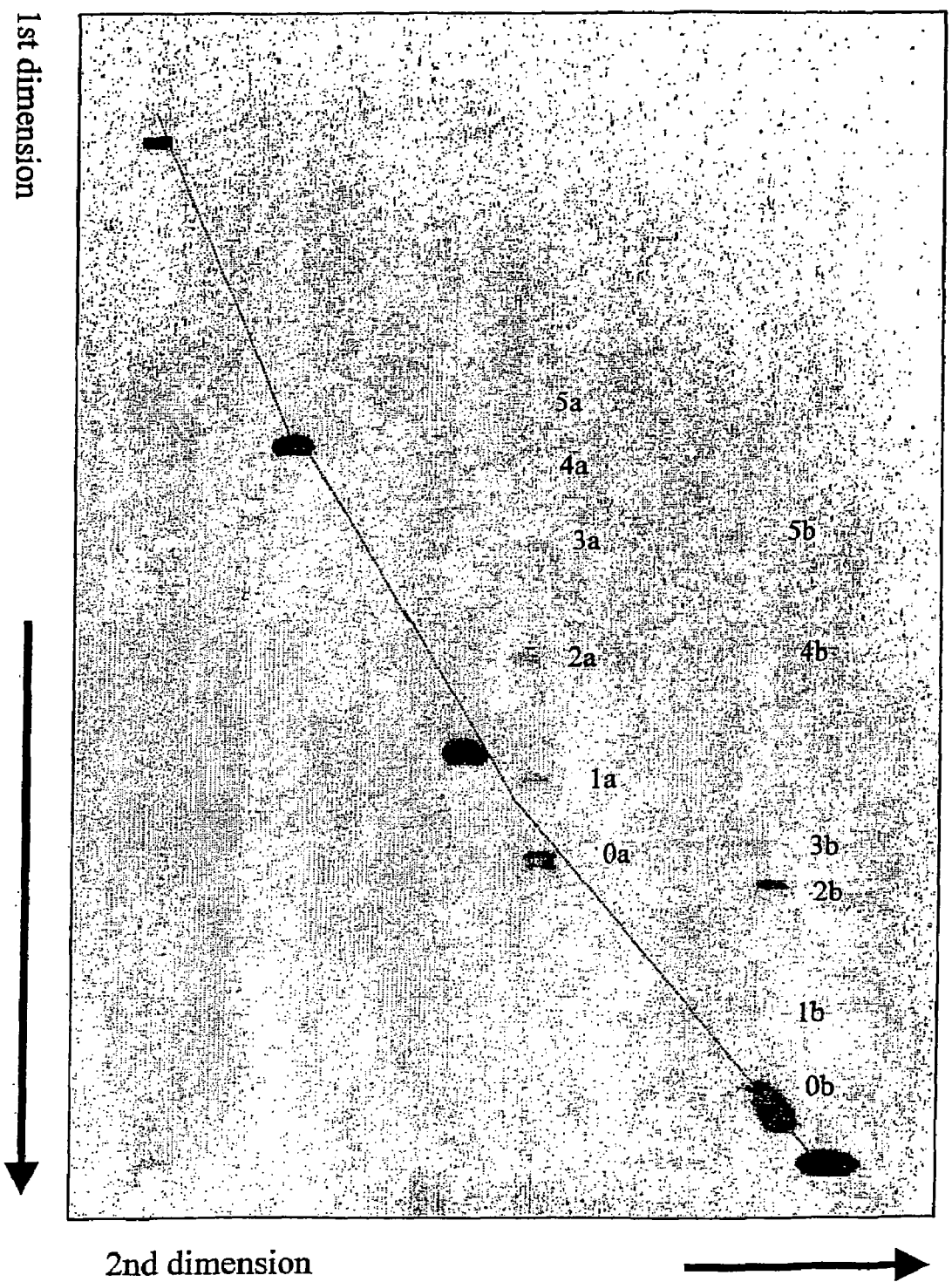
FIG. 2 is a digital photograph of 2-D gel analysis conducted as described in Example 2. The photograph was taken after the second dimension electrophoresis using ethidium bromide as an intercalator and DNA stain. DNA fragments containing 0-5 cytosine bulges either at their center (labeled 0a to 5a) or 15 bp from their end (labeled 0b to 5b) where mixed with perfectly matched linear DNA fragments. Similar results are achieved as described in FIG. 1, that is formation of arc containing the perfectly matched DNA fragments and DNA fragments with bulge structures migrating in front of the arc. DNA fragments containing cytosine bulge at center (labeled 1a to 5a) or near one end (labeled 1b to 5b) both nearly form a vertical line of DNA bands in front of the arc showing that all bulge-containing fragments migrate at the similar rate in the second dimension. In this experiment linear DNA fragments containing 1 to 5 cytosines are separated from linear perfectly matched DNA independently of whether the bulge is at the center or near end of the DNA fragment.

As is shown in FIG. 2, the perfectly matched DNA fragments formed an arc lying diagonal through the gel. DNA fragmetns containing 1 to 5 cytosine bulges at their center clearly migrate in front of the arc. DNA fragmetns containing 1 to 5 cytosine bulges near their end also migrate in front of the arc. Each set of DNA molecules migrate with almost the same rate in the second dimension showing that conformational alterations induced by different bulges result in DNA fragments with similar mobility 5 n the second-dimension electrophoresis.

Example 3

Separation and Detection of Cy5-Labeled Linear DNA Fragments Containing Cytosine Bulges from Perfectly Matched Fluorescein Labeled DNA Fragments in 7×8 cm Gel Format Using Intercalator Approach.

Linear Cy5-labeled DNA fragments containing cytosine bulges were prepared as described in Example 1. These DNA fragments were combined with 100 bp fluorescein ladder (BioRAD) containing 100, 200, 300, 400, 500, 600, 700, 800, 900 and 1000 bp DNA fragments. This DNA mixture was then separated by 2-D gel electrophoresis using 6% polyacrylamide gel. The gel was polymerized in 1×TBE buffer (89 mM Tris base, 89 mM borate, and 2 mM EDTA) for 1 hour. The first dimension gel electrophoresis was done in BioRad Mini Protean II vertical electrophoresis system using 7×8 cm glass sandwich with 1 mm spacers. The gel was run at room temperature for 90 minutes at 20 mA with 1×TBE in both upper and lower buffer chambers. The gel was removed from the glass sandwich and soaked in 100 ml of 1×TBE buffer containing 5 micrograms/ml ethidium bromide. The gel was incubated for 10 min in the buffer and then washed briefly in 100 ml of 1×TBE buffer.

Second dimension gel electrophoresis was done in a Pharmacia Multiphor horizontal electrophoresis system. The gel was run for a total of 45 minutes at 20 mA perpendicular to the first dimension electrophoresis using 1×TBE buffer containing 5 microgram/ml ethidium bromide in both buffer chambers. Connection between electrodes in buffer chambers to gel matrix was achieved with paper electrode wicks. the same gel electrophoresis setup as described in Example 3. After the second dimension gel electrophoresis the gel matrix was washed in 200 ml of 1×TBE for 5 min.

Figure 3:
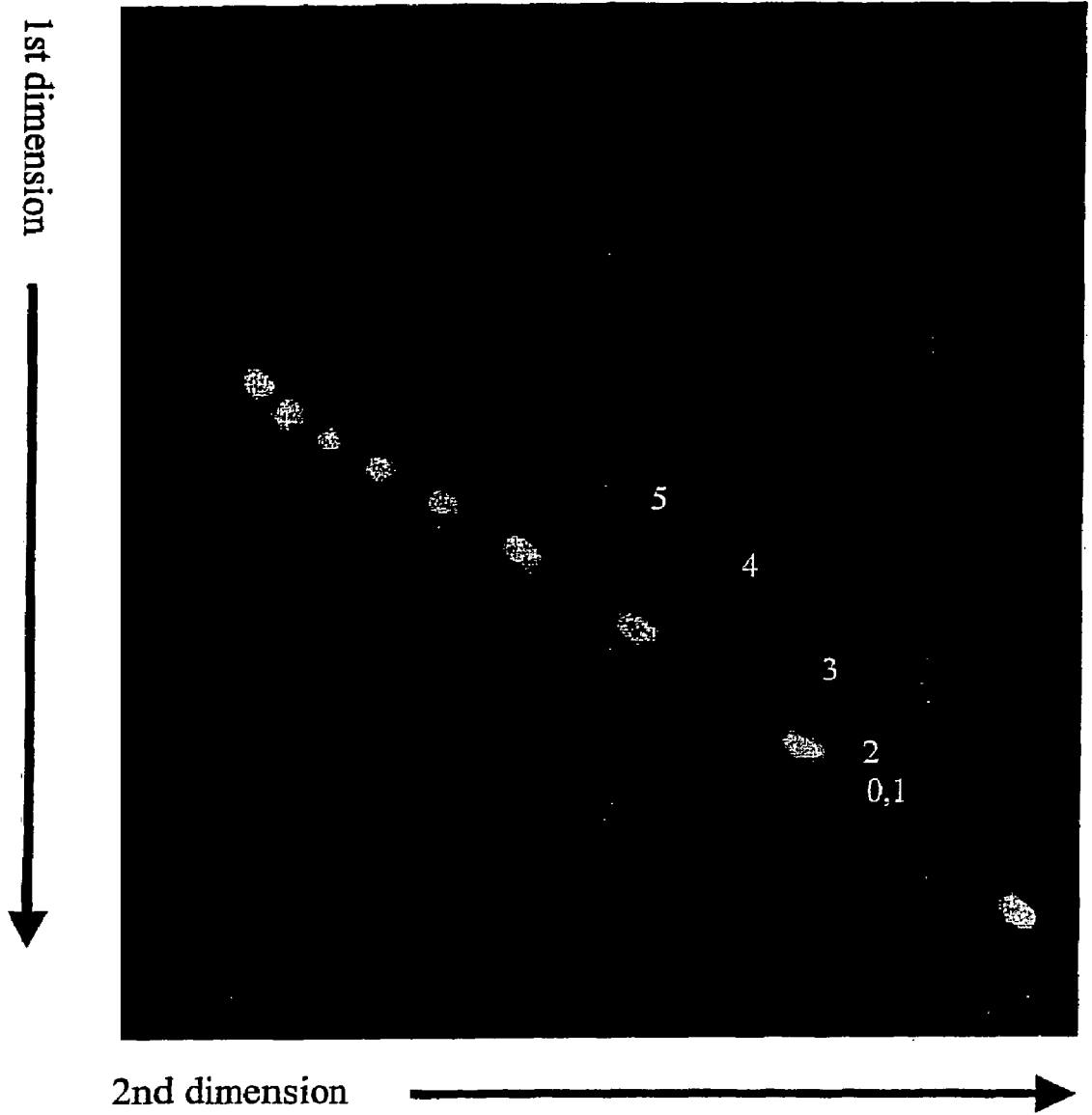
FIG. 3 is a two-color fluorescent image of 2-D gel analysis conducted according to Example 3. Linear perfectly matched DNA fragments are labeled with fluorescein dye resulting in green bands in the figure. The perfectly matched DNA fragments form a diagonal line lying through the gel. DNA fragments containing 0 to 5 cytosine bulge at the center are labeled with Cy5 dye resulting in red DNA bands. In this system, that utilizes 7×8 cm gels, separation is achieved between perfectly matched DNA fragments and DNA fragments containing bulges in the size range of 3 to 5 bases.

Fluorescent detection of DNA fragments was carried out using fluorescence-scanning mode of the AP Biotech's Typhoon 8600 variable mode imager using excitation wavelength 633 nm and the 670BP30 emission filter for Cy5 detection and excitation wavelength 532 nm and the 536SP emission filter for fluorescein detection. As shown in FIG. 3, the perfectly matched DNA fragments formed an arc lying diagonal through the gel. DNA fragments containing 3 to 5 cytosine bulges clearly displaced in front of the arc but the 1 and 2 cytosine bulges were not resolved in this particular gel matrix from its perfectly matched DNA.

Example 4

Separation and Detection of Linear DNA Fragments Containing Cytosine Bulges at their Center from Complex Genomic Representation Using Intercalator Approach.

Linear Cy5 labeled DNA fragments containing cytosine bulges were prepared as described in Example 1.

DNA sample from whole blood from one individual was isolated and, digested with BstY I and purified. Adaptors were ligated to the restriction fragments. PCR using adaptor specific primer and Cy-5 labeled Alu 3' specific primer with internal Bbs I site was done and the resulting Alu 3' fragments were purified using GFX™ columns, then digested with Bbs I and BstY I and purified using GFX™ (see PCT/US99/24984 to Yale University).

Bulge containing DNA fragments were mixed with 2 µl of Alu flank fragments. This DNA mixture was then separated by 2-D gel electrophoresis using 8% polyacrylamide gel. The gel was polymerized in 1×TBE buffer (89 mM Tris base, 89 mM borate, and 2 mM EDTA) for 1 hour. The first dimension gel electrophoresis was done in BioRad Mini Protean II vertical electrophoresis system using 7×8 cm glass sandwich with 1 mm spacers. The gel was run at room temperature for 90 minutes at 20 mA with 1×TBE in both upper and lower buffer chambers. The gel was removed from the glass sandwich and soaked in 100 ml of 1×TBE buffer containing 5 micrograms/ml ethidium bromide. The gel was incubated for 10 min in the buffer and then washed briefly in 100 ml of 1×TBE buffer.

Second dimension gel electrophoresis was done in a Pharmacia Multiphor horizontal electrophoresis system. The gel was run for a total of 60 minutes at 20 mA perpendicular to the first dimension electrophoresis using 1×TBE buffer containing 5 microgram/ml ethidium bromide in both buffer chambers. Connection between electrodes in buffer chambers to gel matrix was achieved with paper electrode wicks the same gel electrophoresis setup as described in Example 3. After the second dimension gel electrophoresis the gel matrix was washed in 200 ml of 1×TBE for 5 min.

Figure 4:
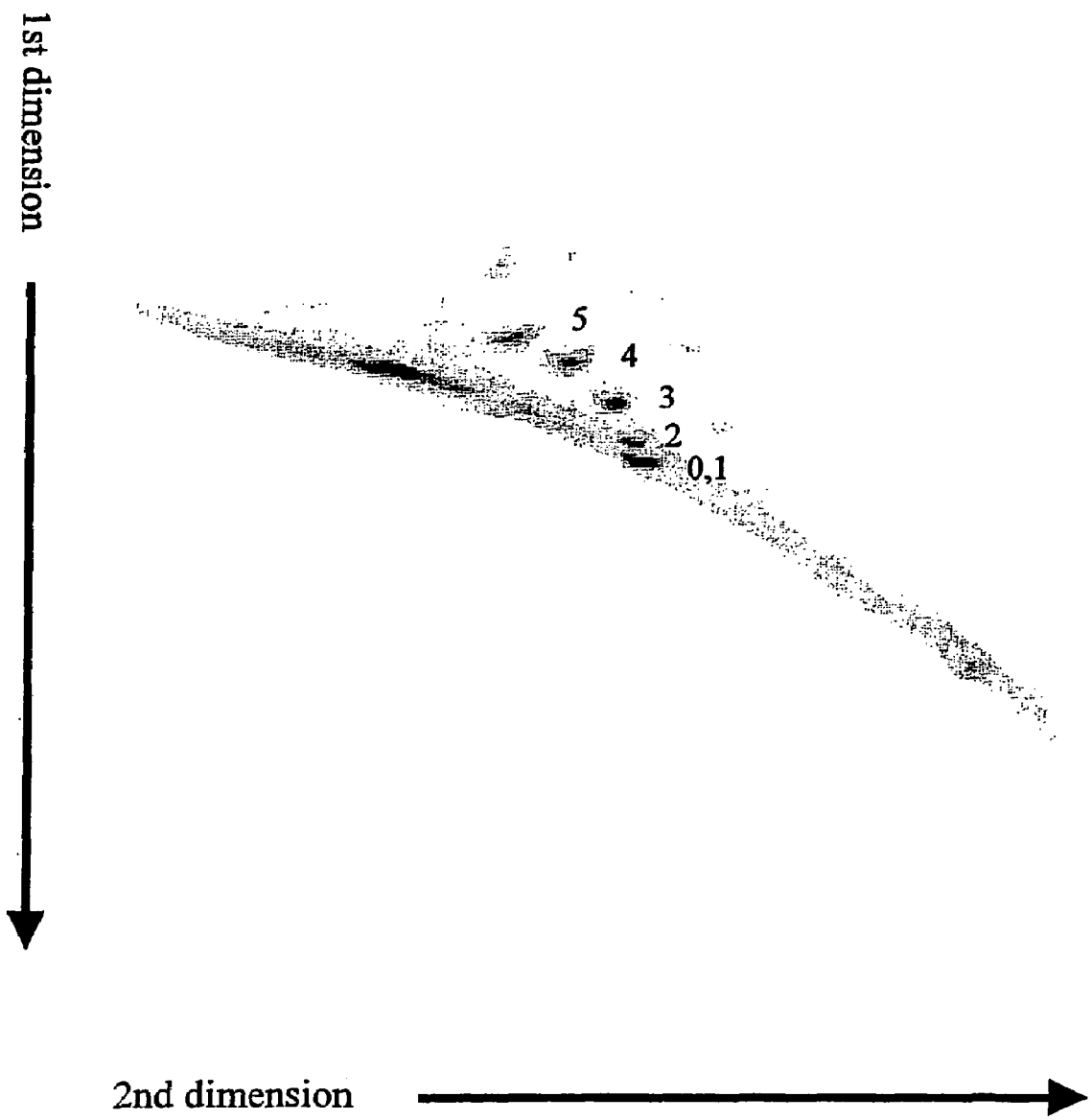
FIG. 4 is an image of 2-D gel analysis conducted as described in Example 4. Before the electrophoresis, linear DNA fragments containing bulges in the size range of 1-5 cytosines were mixed with a complex human genomic representation holding several hundred thousand linear DNA fragments. An arc is formed containing the complex genomic representation and DNA fragments with either 1 or 2 base bulge which are not resolved in this setup. Due to the great complexity of the representation, individual fragments in the arc are not resolved. DNA fragments containing bulges in the size range of 3 to 5 bases are placed in front of the arc after the 2-D electrophoresis.

Fluorescent detection of DNA fragments was carried out using fluorescence-scanning mode of the AP Biotech's Typhoon 8600 variable mode imager using excitation wavelength 633 nm and the 670BP30 emission filter for Cy5 detection and excitation wavelength 532 nm and the 536SP emission filter for fluorescein detection. As shown in FIG. 4, the Alu flank DNA fragments formed an arc lying diagonal through the gel. DNA fragments containing 3 to 5 cytosine bulges clearly displaced in front of the arc but the 1 and 2 cytosine bulges were not resolved in this particular gel matrix from its perfectly matched Alu flank DNA fragments.

Example 5

Separation of DNA Fragment Containing A-Tract from Perfectly Matched DNA Fragments Using Intercalator Approach.

The restriction fragments of a phi-x 174 Hae III digest contain one 281 bp fragment, which is curved because of an A-tract. To demonstrate the efficiency of the methods of inventions we separated this fragment from the rest of restriction fragments in the phi-x 174 Hae III digest using the 2-D gel electrophoresis system. A 298 bp fragment containing a 3 cytosine bulge at the center, prepared as described in Example 1, was added as a control to the phi-x 174 Hae III digest to demonstrate efficiency of 2-D gel electrophoresis system using the MDE™ gel matrix (FMC bioproducts) which is a well-known matrix for heteroduplex analysis.

The gel matrix consisted of 0.75×MDE solution. The gel was polymerized in 1×TBE buffer (89 mM Tris base, 89 mM borate, and 2 mM EDTA) for 1 hour. The first dimension gel electrophoresis was done in BioRad Mini Protean II vertical electrophoresis system using 7×8 cm glass sandwich with 1 mm spacers. The gel was run at room temperature for 90 minutes at 20 mA with 1×TBE in both upper and lower buffer chambers. The gel was removed from the glass sandwich and soaked in 100 ml of 1×TBE buffer containing 5 micrograms/ml ethidium bromide. The gel was incubated for 10 min in the buffer and then washed briefly in 100 ml of 1×TBE buffer.

Figure 5:
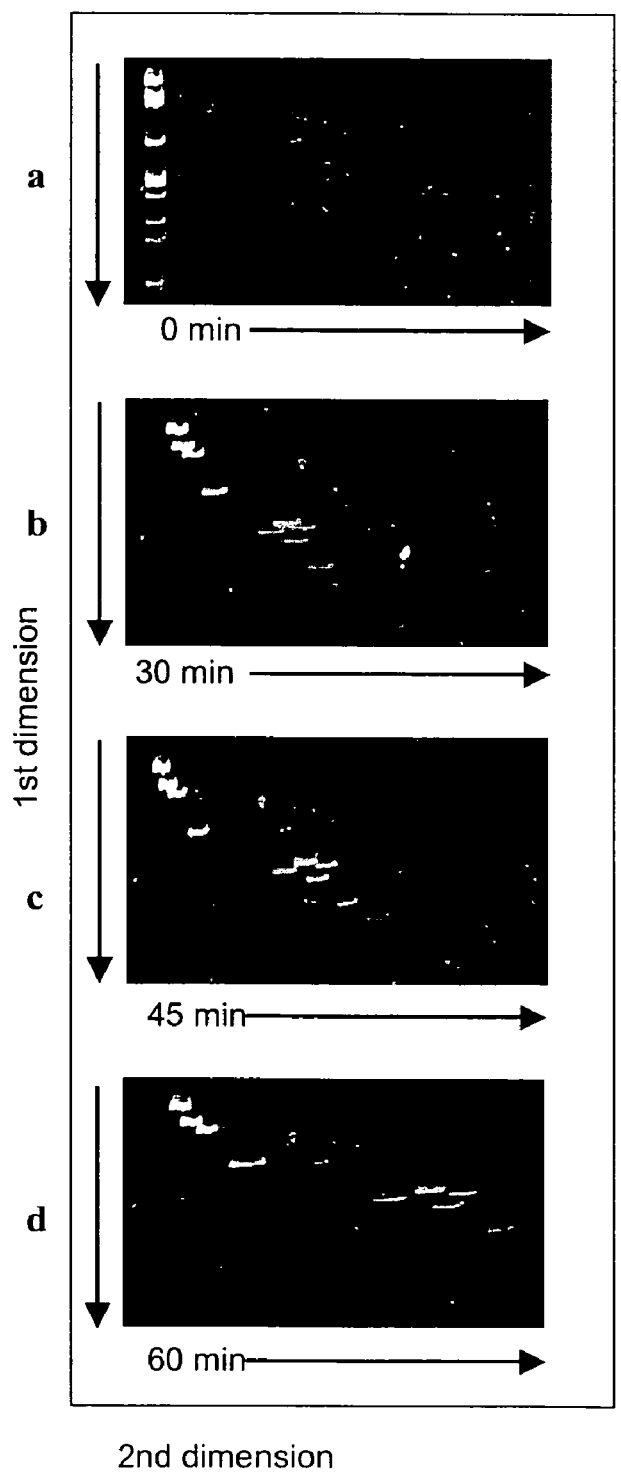
FIGS. 5a-d are digital photographs of 2-D gel analysis conducted as described in Example 5. Photographs were taken after the first dimension electrophoresis (a) and then at interim time points of 30 min (b), 45 min (c), and 60 min (d) of second dimension electrophoresis.

Second dimension gel electrophoresis was done in a Pharmacia Multiphor horizontal electrophoresis system. The gel was run for a total of 60 minutes with interim photographs taken at 0, 30, and 45 minutes at 20 mA perpendicular to the first dimension electrophoresis using 1×TBE buffer containing 5 microgram/ml ethidium bromide in both buffer chambers. Connection between electrodes in buffer chambers to gel matrix was achieved with paper electrode wicks. After the second dimension gel electrophoresis the gel matrix was placed in UVP GDS-8000 gel documentation system for UV detection of ethidium bromide stained DNA fragments. As shown in FIG. 5, the DNA fragments containing normal secondary structure form an arc lying diagonal through the gel. DNA fragments containing unusual secondary structures clearly migrate in front of the arc where the slower migrating band is the 3 bases cytosine bulge fragment and the faster migrating band is the DNA fragment containing A-tract. By increasing the time of second dimension electrophoresis further separation can be achieved (compare FIG. 2b to d).

Example 6

Separation of DNA Fragment Containing UV-Lesions from Intact DNA Fragments Using Intercalator Approach.

For efficient formation of photoproducts we used following technique. 545 bp PCR product in (0.3 pmol/μl in 10 mM Tris HCl pH 8 and 20 mM acetophenon) was UV irradiated at 300 nm for 0, 5, 15, 30, and 60 min using UVP Ultraviolet Transilluminator. Small droplets (3 μl) of were placed at the bottom of Petridish. Water condensed environment was formed by attaching wet tissue paper into the dish sides. The Petridish was then put upside down on the UV-source. The Petridish was covered with a plastic bag containing ice cubes for efficient cooling of the droplet. Care was taken that irradiated PCR products were not exposed to any light source. After UV exposure, 3 μl of DNA fragment containing UV-lesions were added to 1 μl of to the phi-x 174 Hae III digest.

This DNA mixture was then separated by 2-D gel electrophoresis using 9% polyacrylamide gel. The gel was polymerized in 0.5×TBE buffer (89 mM Tris base, 89 mM borate, and 2 mM EDTA) for 1 hour. The first dimension gel electrophoresis was done in BioRad Mini Protean II vertical electrophoresis system using 7×8 cm glass sandwich with 1 mm spacers. The gel was run at room temperature for 45 minutes at 20 mA with 1×TBE in both upper and lower buffer chambers. The gel was removed from the glass sandwich and soaked in 100 ml of 1×TBE buffer containing 5 micrograms/ml ethidium bromide. The gel was incubated for 10 min in the buffer and then washed briefly in 100 ml of 1×TBE buffer.

Figure 6:
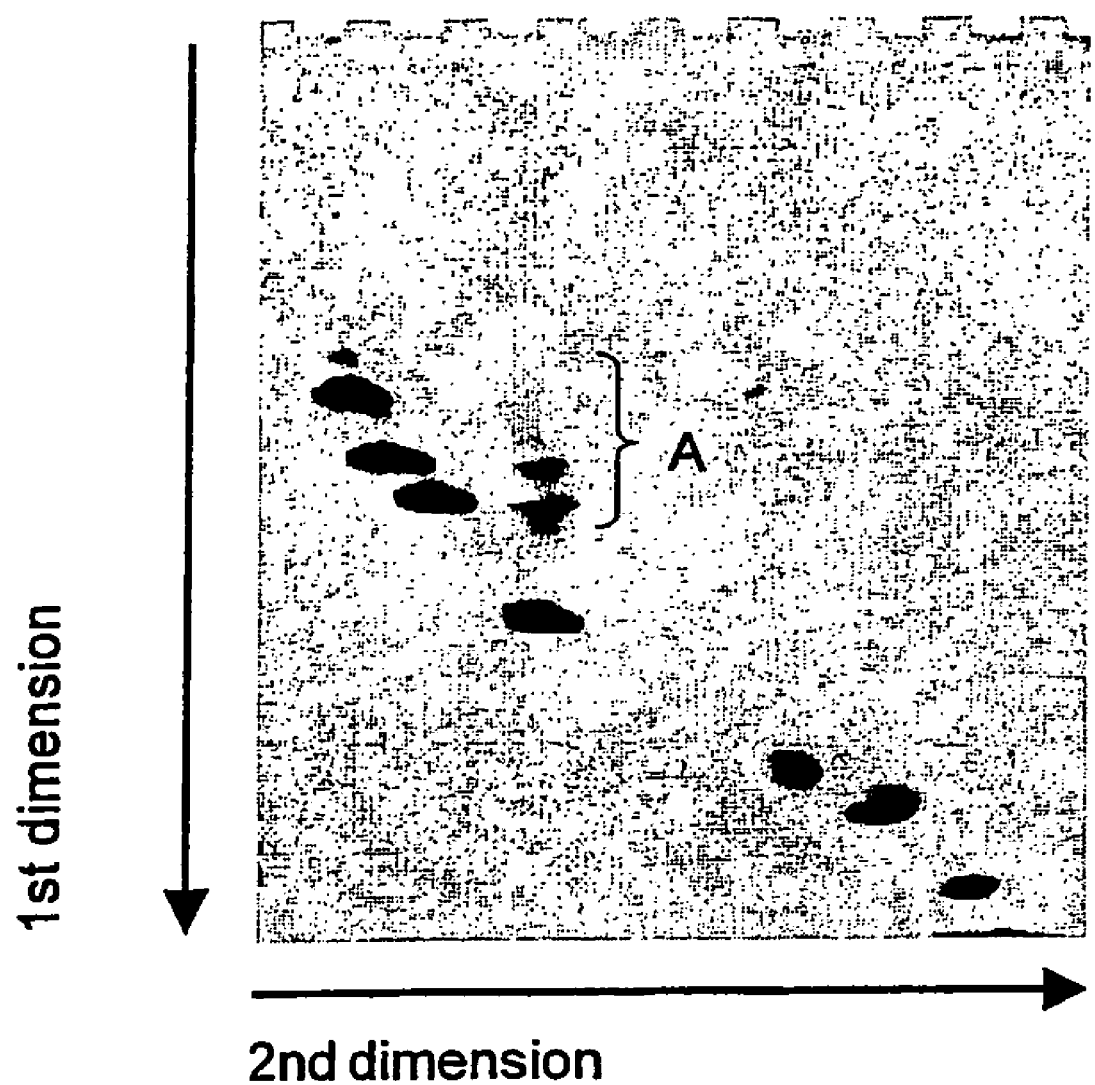
FIG. 6 is a digital photograph of 2-D gel analysis conducted as described in Example 6. A 545 bp PCR product containing unspecific UV-lesions was mixed with intact linear DNA fragments and separated using 2-D gel system using the intercalator approach. The gel shows formation of an arc containing intact linear DNA fragments. In front of the arc, several DNA spots that almost form a vertical line are clearly detected. The formation of UV-lesion was not specific and therefore broad vertical line is detected in front of the arc due to different amount of UV-lesions in each molecule. The label 'A' refers to these 545 bp DNA containing CPD damage at varible sites

Second dimension gel electrophoresis was done in a Pharmacia Multiphor horizontal electrophoresis system. The gel was run for a total of 90 minutes at 15 mA perpendicular to the first dimension electrophoresis using 1×TBE buffer containing 5 microgram/ml ethidium bromide In both buffer chambers. Connection between electrodes in buffer chambers to gel matrix was achieved with paper electrode wicks. After the second dimension gel electrophoresis the gel matrix was placed in UVP GDS-8000 gel documentation system for UV detection of ethidium bromide stained DNA fragments. As shown in FIG. 6, the intact DNA fragments form an arc lying diagonal through the gel. DNA fragments containing UV-lesions clearly migrate in front of the arc. Due to non-specific formation of UV-lesion in the DNA fragment a broad band UV-lesion containing DNA fragments is separated.

Example 7

Separation of DNA Fragments Containing Single Nick from Intact DNA Fragments Using Intercalator Approach.

Hind III digested phi-x plasmid are treated with the Nicking endonuclease N.BstNB I (New England Biolabs). N.BstNB I hydrolyze only one strand of the duplex in sequence specific manner. After the N.BstNB I treatment 4 out of 10 DNA fragments contains specific nicks; 770 bp fragment nicked 85 bp from 5' end, 345 bp fragment nicked 181 bp from 5' end, 335 bp fragment nicked 32 bp and 71 bp from 5' end and 291 bp fragment nicked 23 bp and 256 bp from 5' end.

All ten fragments are then separated by 2-D gel electrophoresis. The gel matrix consisted of 8% polyacrylamide prepared from 29:1 acrylamide:bisacrylamide mixture containing 7M urea. The gel was polymerized in 1×TBE buffer for 1 hour. First dimension gel electrophoresis was done in BioRad Mini Protean II vertical electrophoresis system using 7×8 cm glass sandwich with 1 mm spacers. The gel was run at room temperature for 45 minutes at 20 mA with 1×TBE in both upper and lower buffer chambers. The gel was removed from the glass sandwich and three times soaked for 10 minutes in 100 ml of 1×TBE buffer. Then the gel was soaked in 100 ml of 1×TBE buffer containing 5 micrograms/ml ethidium bromide for 10 min and washed briefly in 100 ml of 1×TBE buffer.

Figure 7:
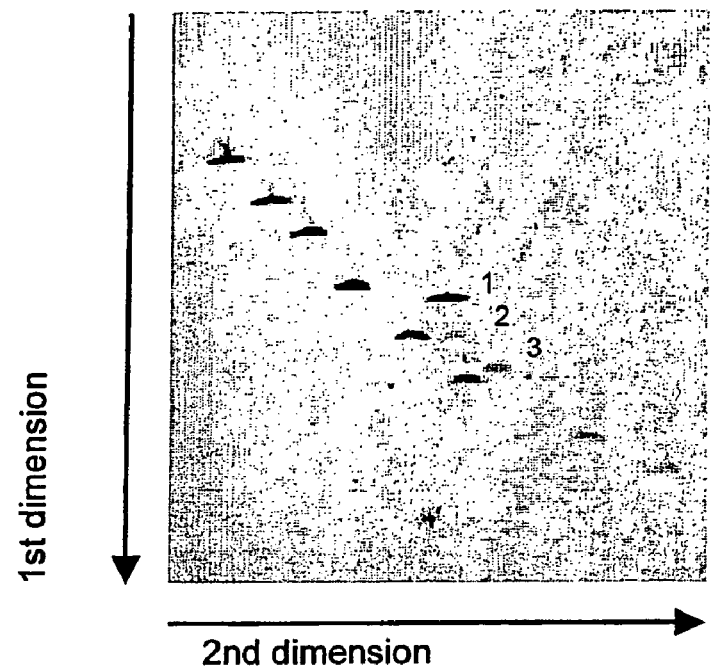
FIG. 7 is an image of 2-D gel analysis conducted as described in Example 7. HindIII digested phi-x plasmid was treated with the Nicking endonuclease N.BstNB I. Then the linear DNA fragments were separated using 2-D gel electrophoresis. Intact linear DNA fragments form an arc. Three DNA fragments with one strand hydrolyzed in sequence specific manner clearly travel in front of the arc of intact DNA fragments thus showing separation between intact and nicked DNA fragments in a system using 7M urea in the first dimension and the intercalator approach.

Second dimension gel electrophoresis was done in a Pharmacia Multiphor horizontal electrophoresis system. The gel was run for a total of 45 minutes at 5 W perpendicular to the first dimension electrophoresis using 1×TBE buffer containing 5 microgram/ml ethidium bromide in both buffer chambers. Connection between electrodes in buffer chambers to gel matrix was achieved with paper electrode wicks. After the second dimension gel electrophoresis the gel matrix was placed in UVP GDS-8000 gel documentation system for UV detection of ethidium bromide stained DNA fragments. As shown in FIG. 7, the intact DNA fragments form an arc lying diagonal through the gel. Three DNA fragments (345 bp, 335 bp and 291 bp) containing nicks clearly migrate in front of the arc.

Example 8

Separation and Detection of Cy5 Labeled DNA Fragment Containing Binding Site for PvuII from Perfectly Matched DNA Fragments in 7×8 Gel Format Using Intercalator Approach.

Double digestion of pUC18 with NarI and AvaI led to the formation of two fragments; 198 bp linear DNA fragment containing PvuII recognition site 72 bp from 5' end, and 2488 bp fragment containing PvuII recognition site 196 bp from 5' end. Products were Cy5 labeled by Klehow extension. These two fragments were mixed with phi-X/HaeIII digested DNA (no recognition site for PvuII) and PvuII in binding reaction. Binding reactions (20 µl) contained PvuII (1 nM), 10 nM of DNA fragments containing PvuII sites, 500 ng phi-x/HaeIII digested DNA, 10 mM Tris (pH 8.0), 50 mM NaCl, 1 mM DDT, 1 mM EDA, 10 mM $CaCl_2$, 30 µg/ml BSA, and 7.5% glycerol. A binding reaction was incubated at RT for 20 min prior to 2-D gel electrophoresis.

The gel matrix consisted of 9% polyacrylamide prepared from 29:1 acrylamide:bisacrylamide mixture containing 10 mM $CaCl_2$. The gel was polymerized in 0.5×TBE buffer for 1 hour. First dimension gel electrophoresis was done in BioRad Mini Protean II vertical electrophoresis system using 7×8 cm glass sandwich with 1 mm spacers. The gel was run at 4° C. for 120 minutes at 5 W with 0.5×TBE containing 10 mM $CaCl_2$ in both upper and lower buffer chambers. The gel was removed from the glass sandwich and three times soaked for 10 minutes in 100 ml of 1×TBE buffer. Then the gel was soaked in 100 ml of 1×TBE buffer containing 5 micrograms/ml ethidium bromide for 10 min and washed briefly in 100 ml of 1×TBE buffer.

Second dimension gel electrophoresis was done in a Pharmacia Multiphor horizontal electrophoresis system. The gel was run for a total of 55 minutes at 5 W perpendicular to the first dimension electrophoresis at RT using 1×TBE buffer containing 5 microgram/ml ethidium bromide in both buffer chambers. Connection between electrodes in buffer chambers to gel matrix was achieved with paper electrode wicks.

Figure 8:
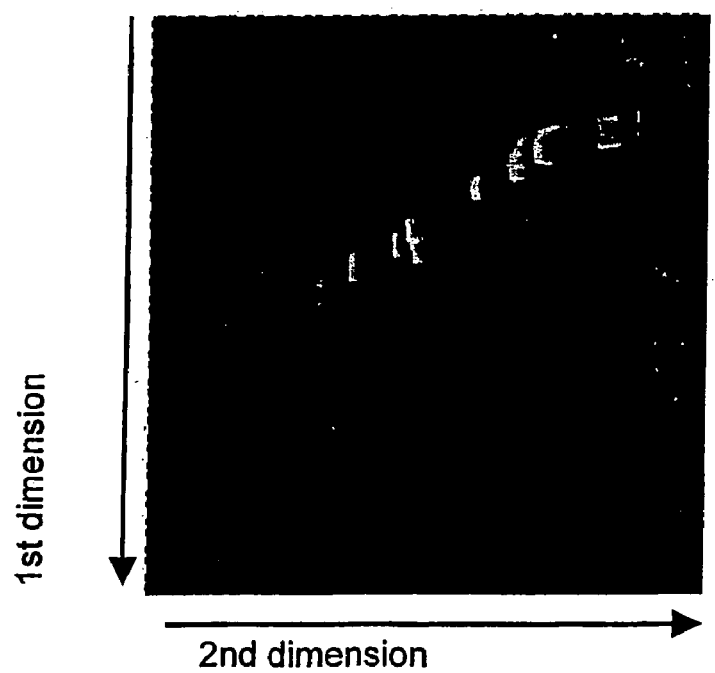
FIG. 8 is a two color fluorescent image of 2-D gel analysis conducted as described in Example 8. A protein-DNA binding assay between PvuII and complex mixture linear DNA fragments is performed. Two of the DNA fragments in the mixture contains PvuII recognition sites and these fragments are specifically labeled with Cy5. After given incubation time the binding reaction separated using to 2-D gel electrophoresis using the intercalator approach. DNA fragments which do not form interaction with PvuII shape an arc lying through the gel (green bands). Unbound DNA fragments with recognition site are also placed in the arc (red bands). DNA fragment bound to PvuII clearly travel in front of the arc (red band) thus showing separation between unbound and bound DNA fragments in the system. The 2488 bp fragment containing PvuII recognition site 196 bp from 5' end is to large to resolve in this gel.

Fluorescent detection of DNA fragments was carried out using fluorescence-scanning mode of the AP Biotech's Typhoon 8600 variable mode imager using excitation wavelength 633 nm and the 670BP30 emission filter for Cy5 detection and excitation wavelength 532 nm and the 610BP30 emission filter for etidium bromide detection. As shown in FIG. 8, the perfectly matched DNA fragments without binding site and unbound 196 bp DNA fragment containing the binding site formed an arc lying diagonal through the gel. A 196 bp DNA fragments containing binding site for PvuII is clearly displaced in front of the arc but the 2455 bp fragment was to long to be resolved in this particular gel matrix from other unbound linear DNA fragments.

Example 9

Separation and Detection of Cy5 Labeled DNA Fragments Containing 4 Cytosine Bulge from Perfectly Matched Fluorescein Labeled DNA Fragments in 7×8 Gel Format Using Denaturating Approach A 298 bp fragment with 5' Cy5 label containing a 4 cytosine bulge at the center was prepared as described in Example 1. The bulge-containing fragment was added to Fluorescein Low Range DNA Standards (BioRad) which contained ten perfectly matched DNA fragments, ranging from 75 to 1632 bp, and then separated by 2-D gel electrophoresis. The gel matrix consisted of 8% polyacrylamide prepared from 29:1 acrylamide:bisacrylamide mixture. The gel was polymerized in 1×TBE buffer for 1 hour. First dimension gel electrophoresis was done in BioRad Mini Protean II vertical electrophoresis system using 7×8 cm glass sandwich with 1 mm spacers. The gel was run at room temperature for 90 minutes at 20 mA with 1×TBE in both upper and lower buffer chambers. The gel was removed from the glass sandwich and soaked in 100 ml of 1×TBE buffer containing 7M urea. The gel was incubated for 10 min in the buffer and then kept at 94° C. for 5 minutes. The gel was heated in a Plexiglas sandwich to prevent drying of the gel.

Second dimension gel electrophoresis was done in a Pharmacia Multiphor horizontal electrophoresis system. The gel was run at 20° C. for 1 hour at 20 W perpendicular to the first dimension electrophoresis using 1×TBE buffer in both buffer chambers. Connection between electrodes in buffer chambers trough gel matrix was achieved with paper electrode wicks.

Figure 9:
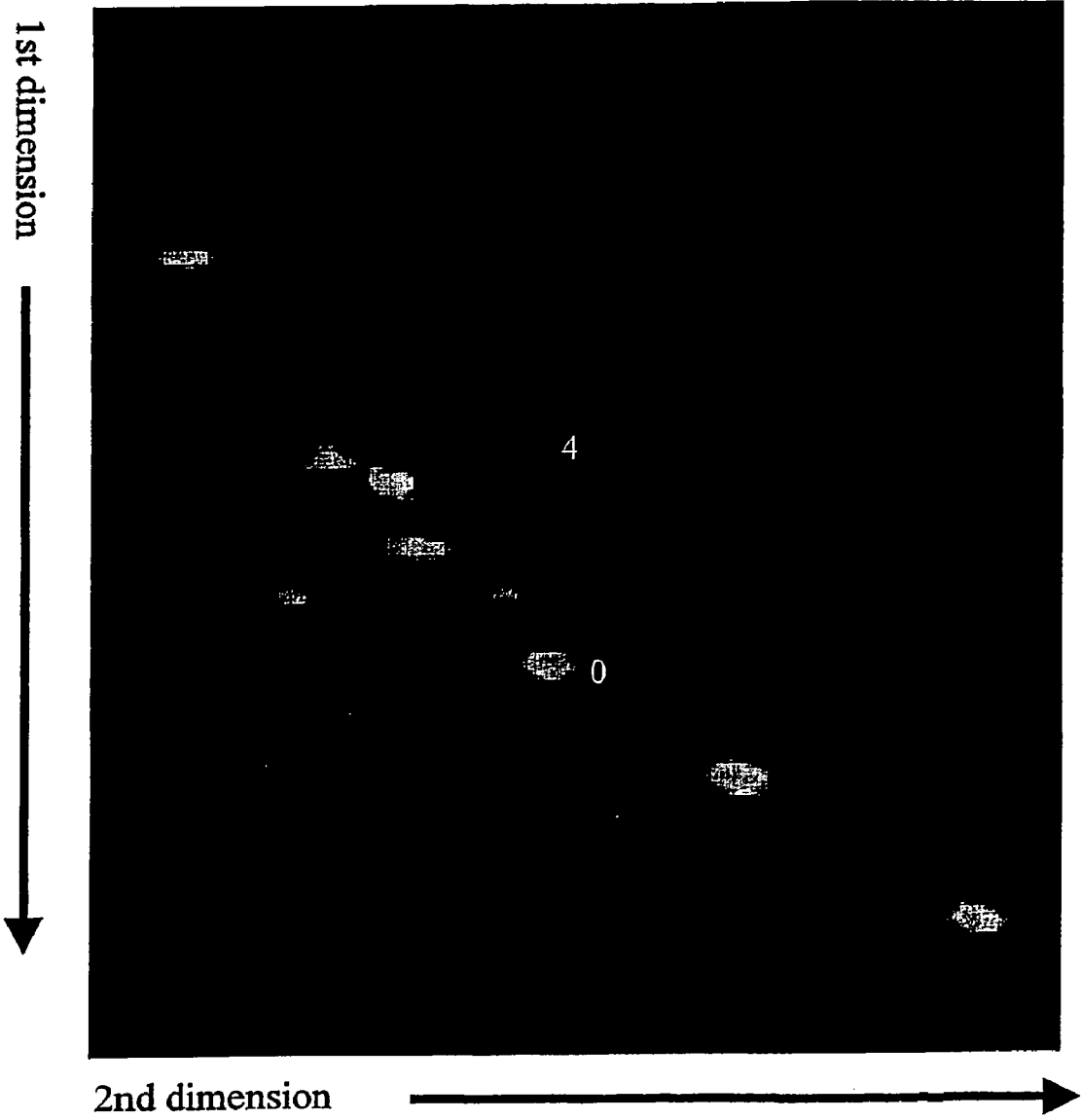
FIG. 9 is a copy of a two color fluorescent image of 2-D gel analysis conducted as described in Example 9. Perfectly matched DNA fragments are labeled with fluorescein dye resulting in green DNA bands. The perfectly matched DNA fragments form a diagonal line lying through the gel. DNA fragments containing either 0 or 4 cytosine bulge at the center are labeled with Cy5 dye resulting in red DNA bands (labeled 0 and 4 in the Figure). DNA fragment containing 4 cytosine bulge clearly travel in front of the perfectly matched DNA fragments thus showing separation between perfectly- and mismatched DNA fragments in a system using fully denaturating conditions in the second dimension.

Fluorescent detection of DNA fragments was carried out as described in Example 3. As shown in FIG. 9, DNA strands corresponding to perfectly matched DNA fragments form an arc lying diagonal through the gel (green bands in Figure). DNA strands originating from the four cytosine bulge double stranded DNA fragment (red band in Figure) clearly migrated in front of the arc.

Example 10

Separation and Detection of DNA Fragment Containing 3 Cytosine Bulge from Perfectly Matched DNA Fragments Using Page in First Dimension and Agarose Electrophoresis in the Second Dimension.

A 298 bp fragment containing a 3 cytosine bulge at the center was prepared as described in Example 1. The bulge-containing fragment was added to the restriction fragments of a phi-x 174 Hae III digest that also contain one 281 bp fragment, which is curved because of an A-tract. The mixture was separated by 2-D gel electrophoresis. The first dimension gel matrix consisted of 10% polyacrylamide prepared from 29:1 acrylamide:bisacrylamide mixture. The gel was polymerized in 1×TAE buffer for 1 hour. First dimension gel electrophoresis was done in BioRad Mini Protean II vertical electrophoresis system using 7×8 cm glass sandwich with 1 mm spacers. The gel was run at room temperature for at 20 mA with 1×TAE in both upper and lower buffer chambers until bromophenol blue dye migrated over ⅔ length of gel. For the second dimension electrophoresis a 1.7% agarose gel was casted in 1×TAE. This gel had 1 mm lane lying horizontal near the upper edge of the gel. After first dimension electrophoresis the lane containing DNA was cut from the gel. The PAGE strip was sealed in the lane of the agarose gel using warm agarose.

Figure 10:
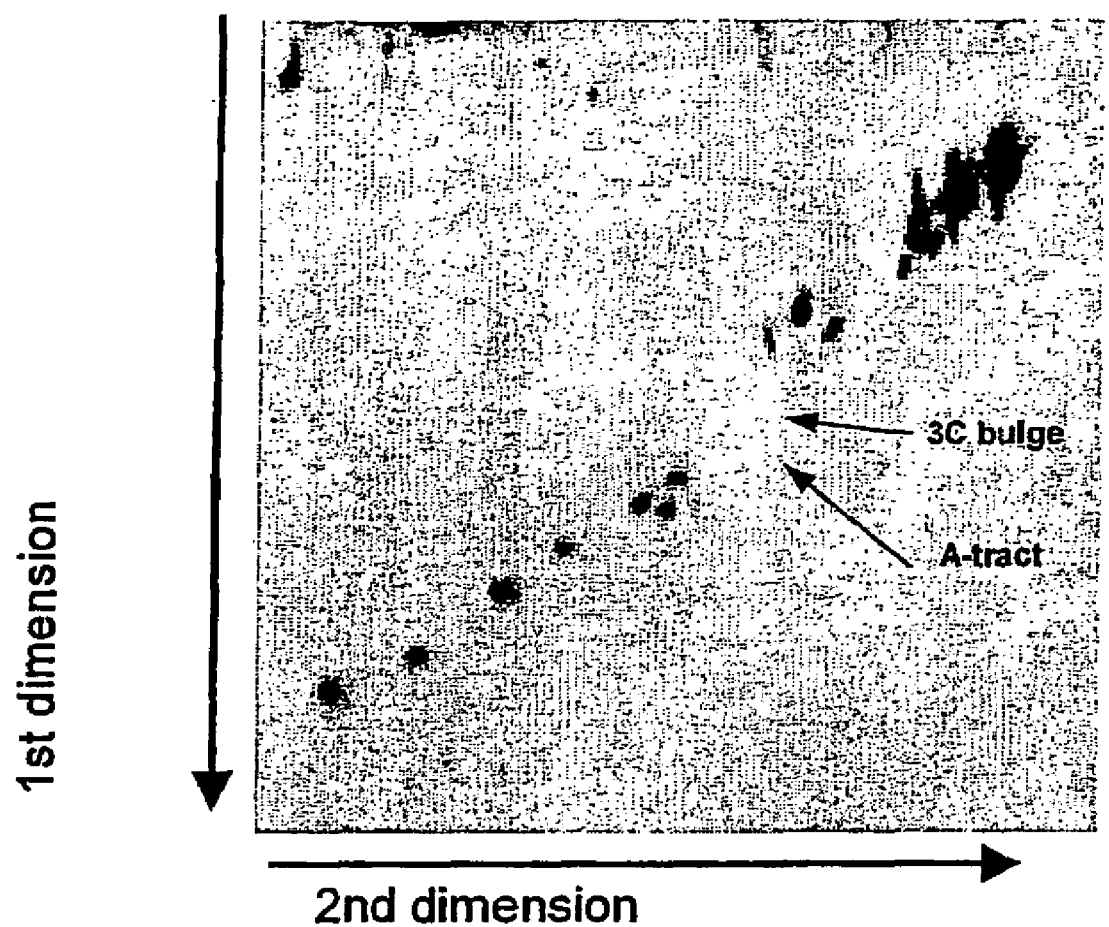
FIG. 10 is a digital photograph of 2-D gel analysis conducted as described in Example 10.

Second dimension gel electrophoresis was done in a horizontal submarine electrophoresis system. The gel was run at 20° C. for 1 hour at 110 V using 1×TAE buffer. After the second dimension gel electrophoresis the gel was placed in UVP GDS-8000 gel documentation system for UV detection of ethidium bromide stained DNA fragments. As shown in FIG. 10, the DNA fragments containing normal secondary structure form an arc lying diagonal through the gel. DNA fragments containing unusual secondary structures clearly migrate in front of the arc where the slower migrating band is the 3 bases cytosine bulge fragment and the faster migrating band is the DNA fragment containing A-tract.

Example 11

Isolation and Characterization of Highly Polymorphic Sequences from the Human Genome.

DNA samples from whole blood from ten individuals were isolated and digested individually with BstY I and purified. Adaptors were ligated to the restriction fragments. PCR using adaptor specific primer and Alu 3' specific primer with internal Bbs I site was done and the resulting Alu 3' flank fragments were purified using GFX™ columns, then digested with Bbs I and BstY I and purified using GFX™ (see PCT/US99/24984 to Yale University). Then 4 micrograms of PCR fragments from each individual were mixed together, precipitated, resuspended in 4 microliters 3×EE buffer, and 35 microliters of mineral oil added on top of the sample. The sample was then heated to 94° C. for 5 min, 1 microliter 5 M NaCl added and incubated in a water bath at 67° C. for 20 hours.

Figure 11A:
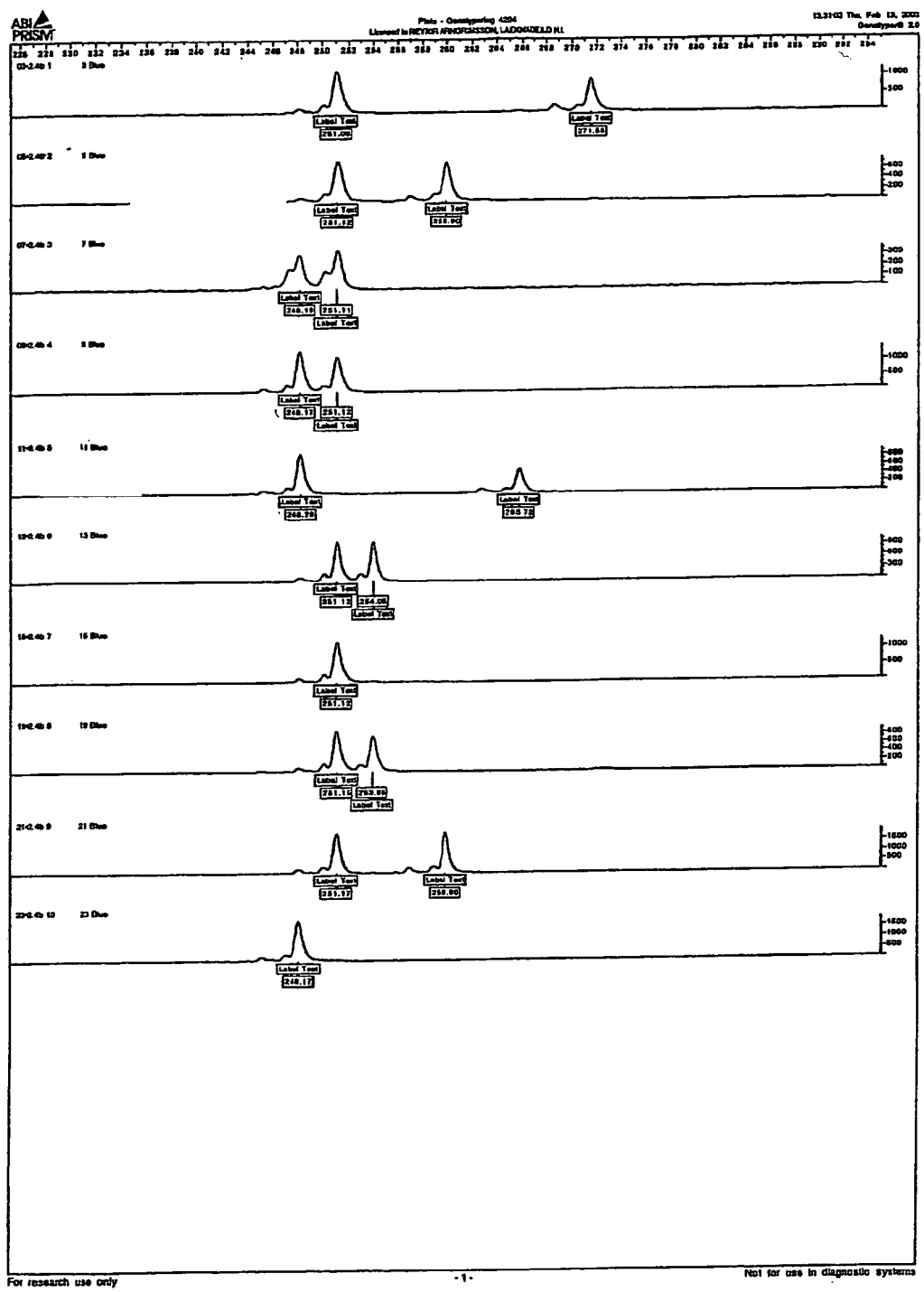
FIGS. 11a-d are examples of genotyping results of PCR sequences obtained in the experiment described in Example 11. The genotype was determined from the same tenanomymous as the samples sequences was originally isolated from using 2-D CDE.
Figure 11B:
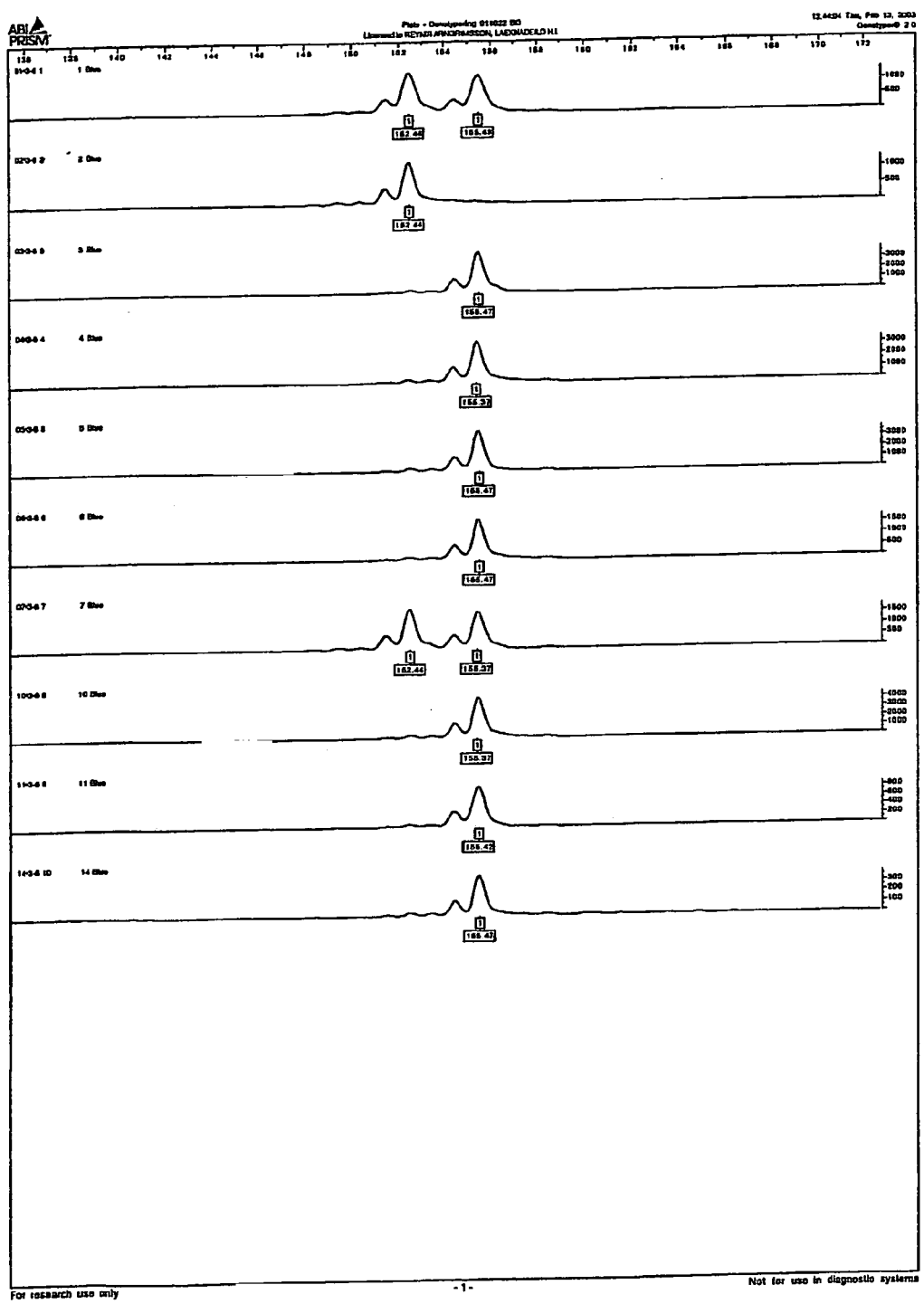
Figure 11C:
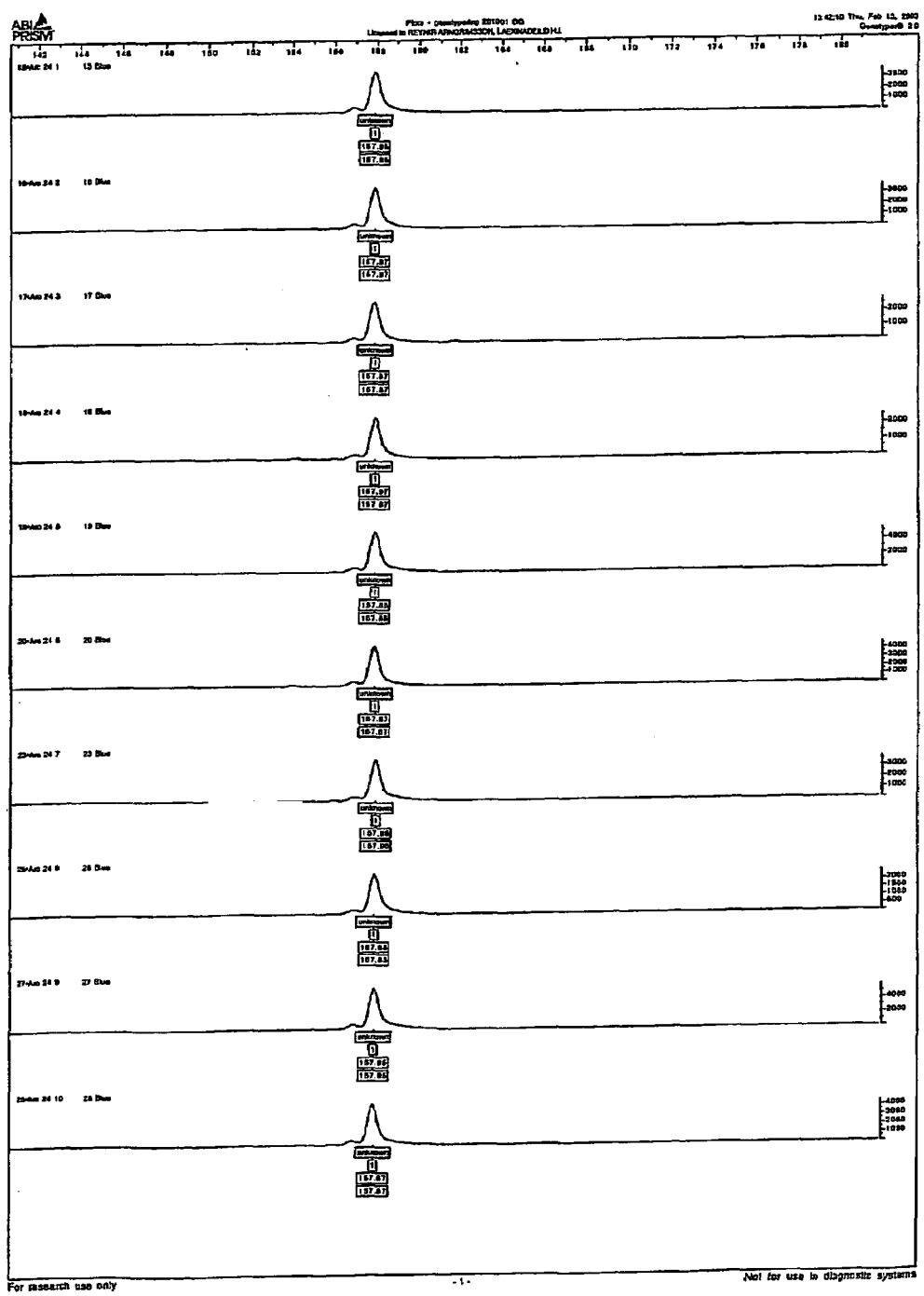

After 20 hours the sample was diluted in 1×TE and tRNA (100 ng/microliter) up to 80 microliters. Adaptors were ligated to 10 microliters or 5 micrograms of reannealed fragments and polymerase used to extend fragments to generate blunt ends. The sample was then subjected to 2-D gel electrophoresis as described above. The DNA migrating in front of the arc and therefore not perfectly matched was cut out of the gel and eluted from the gel in 1×TE at 37° C. over night. We also eluted DNA isolated from the arc which should be perfectly matched. Isolated DNA fragments were further amplified using adaptor specific primers. The resulting PCR fragments were then cloned into plasmid and transformed into E. coli. The inserts were then sequenced (four examples shown in table 1) and specific reverse primers, against Alu specific primer, for genotyping on ABI Prism™ made for 23 clones (14 isolated in front of the arc and 9 from the arc). Sequencing and genotyping on DNA samples from the ten individuals confirmed that 7 of 14 clones isolated in front of the arc were polymorphic between the ten individuals in the orignal pool. (examples of two polymorphic sequences are shown in FIG. 11a and 11b). In contrast none of the nine sequences isolated from the arch itself were polymorphic (examples of two sequences are shown in FIG. 11c and 11b). Therefore, this method is able to isolate and detect new and undiscovered polymorphic sequences in the human genome and other genomes.

TABLE 1

| Insert sequence | Reverse primer for genotyping | Amplicon obtained in genotyping Size (bp) |
| --- | --- | --- |
| 2.4<br>ACAACAACAACAACAACAACGACAACAACAACAACA<br>ACAACAACAACAACAGAAGTGTGACCCAATTTGCAC<br>TGGTGACAATGAAGGCAGCCTTTTCTGGAGGGTTTT<br>TGGGGAAAGGTTTGCACTCTCCTCCCTGGTATCATG<br>GGAGAATCCCAGAAAAAGATGGGATTTGACACCTA<br>GAAGATGCTACTGTGGAAAGCAGGGAGCAGAGAAG<br>GAAAGAAACTCAGTCCAAGAAGACCAT<br>(SEQ ID NO:1)<br>on chromosome 17. | 5'ATGGTCTT<br>CTTGGACTG<br>AGT3'<br>(SEQ ID NO:5) | 248<br>251<br>254<br>259<br>265<br>271 |
| 3.6<br>GGATCCTTCCCTGATCATAGGTAACAACTGATGCTC<br>ACTGTACATCCCTCCCCAGTCAAATTCCTCTC<br>CATGTCCTCCCTTTTGATGTGGTGTCAATCACCCCCA<br>TTTGTATTTTTTACCTTTACTACATTATTATTATTAT<br>TATTATTACTACTATTATTATTATTTGTGTGCATGTG<br>TGTGAG<br>(SEQ ID NO:2)<br>on chromosome 3 | 5'CAGTCAAA<br>TTCGTCTCCA<br>TGTG3'<br>(SEQ ID NO:6) | 152<br>155 |
| R13<br>GGGTGACAAAGCGAGACTCCATCTCAAAAAAAGAA<br>AAAAATGCCCAAATAGAAACTATAAGATGTTATGGC<br>CTTACCTTACTGTCACCACCCATTTCCCCTGTTCATA<br>GCAAGTTTGCCTAA<br>(SEQ ID NO:3)<br>on chromosome 20 | 5'GGCAAACT<br>TGCTATGAA<br>CAG 3'<br>(SEQ ID NO:7) | 158 |
| Arc24<br>GGATCCACAGCCACCACTGCCACATCCATACAAAAA<br>CAACACAGCTCCAGAGTGAACAGAGAGCCGCTCTG<br>GCTTCGATGAGACACCAAATAACCTCGTGTCCCATT<br>TTCTTTATTTTATTTTATTTTTTATTTTGATTTTTT<br>TGCG<br>(SEQ ID NO:4)<br>on chromosome 3 | 5'ACCACTGC<br>CACATCCAT<br>AC 3'<br>(SEQ ID NO:8) | 118 |

Table 1 shows the sequence of 4 cloned fragments (SEQ ID NOS: 1-4) isolated from the 2-D CDE gel, the reverse primer (SEQ ID NOS: 5-8) used for genotyping and the size results of genotyping those sequences from ten individuals. Sequences 2.4 and 3.6 are isolated in front of the arch but sequences R13 and Arch 24 are isolated from the arch itself.

Example 12

Estimation of Reannealing Efficiency for Complex Mixture of Linear DNA Fragments Using Intercalator Approach.

Figure 11D:
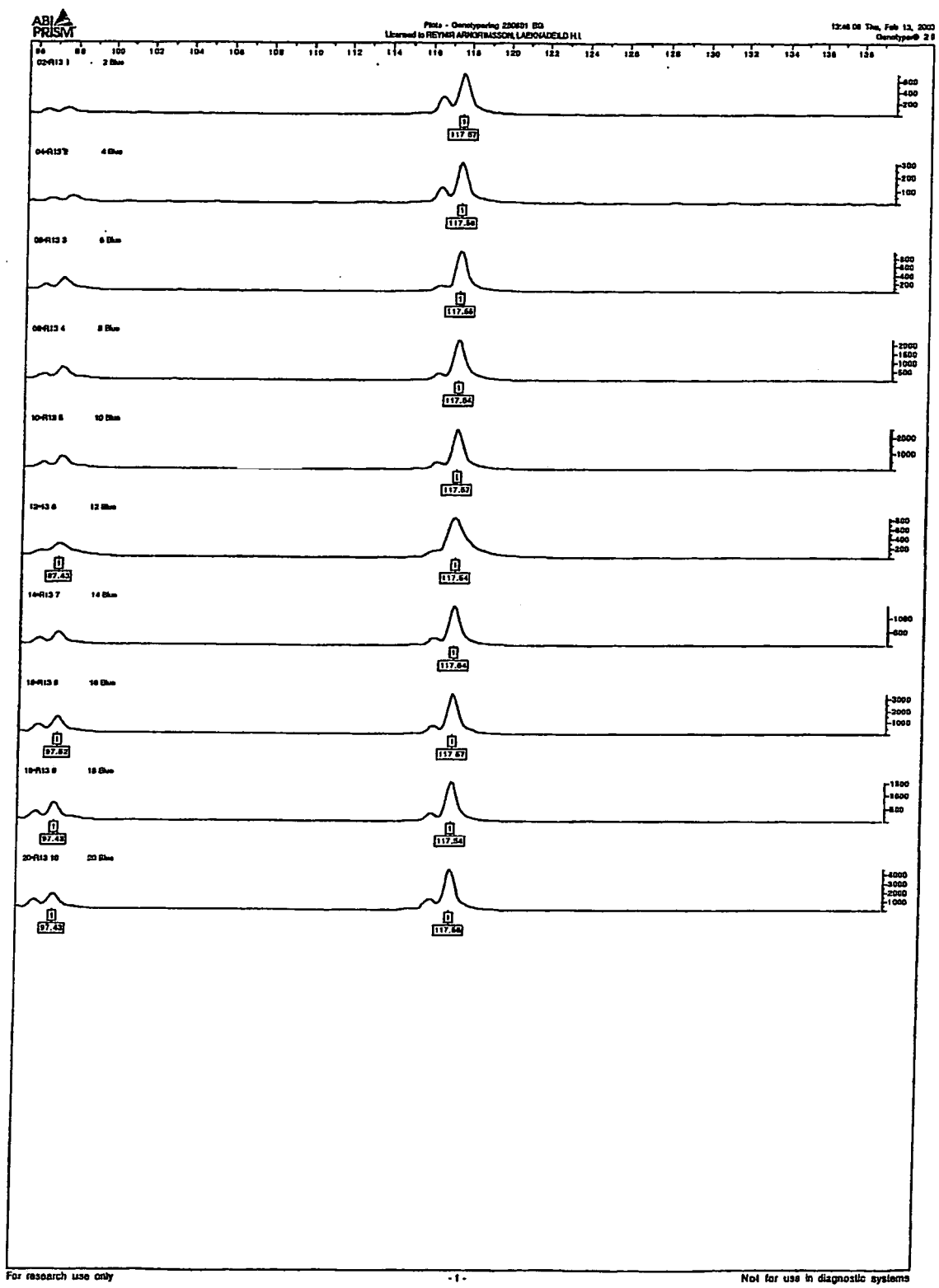
Figure 12:
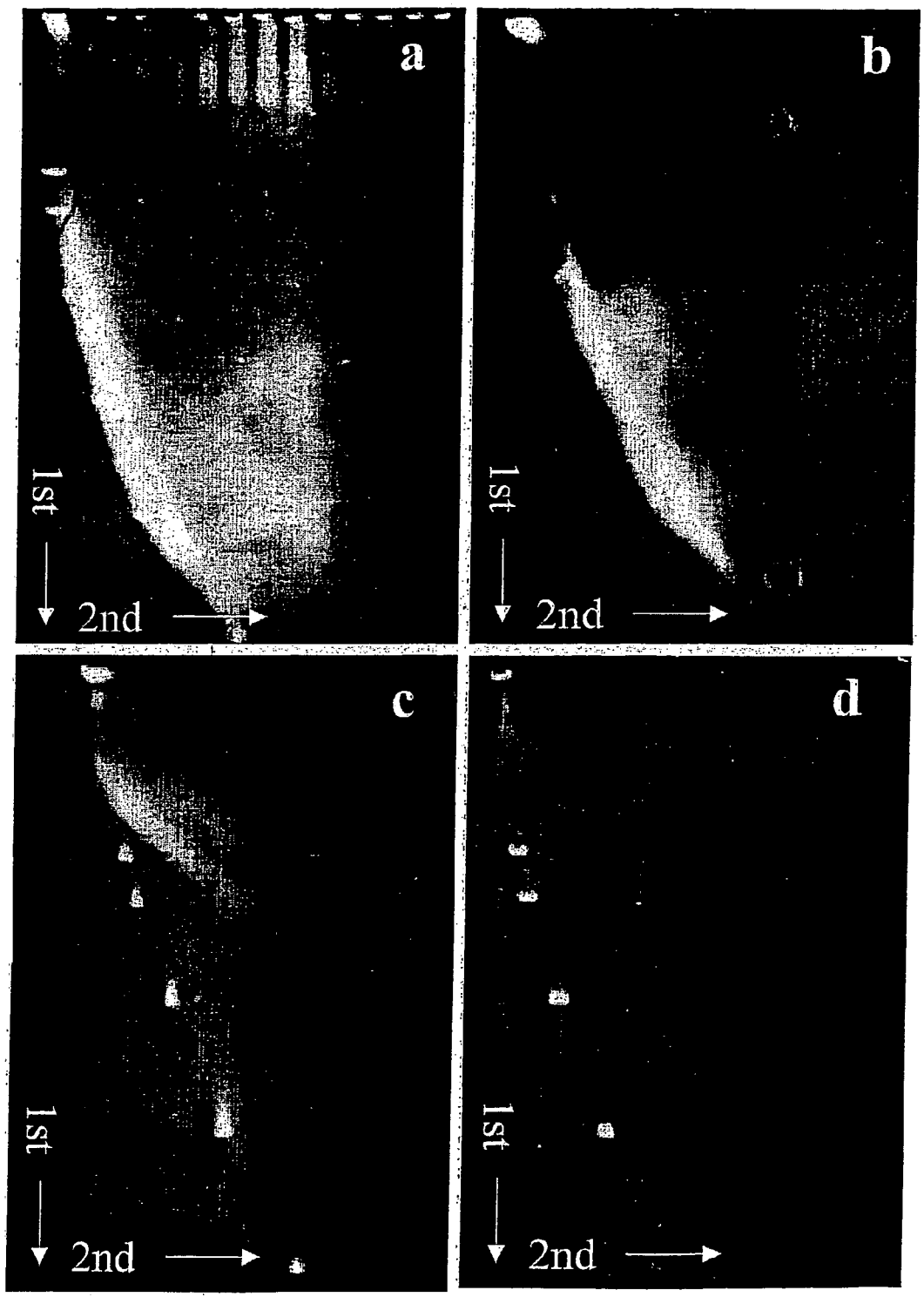
FIGS. 12a-d are digital photographs of UV-exposed 2-D gels conducted as described in Example 12. DNA is visualized using ethidium bromide as a DNA stain.

A pooled sample of Alu 3' fragments from nine individuals was obtained with specific PCR as described in Example 11. The mixture was divided into three parts. One was left untreated, another was reannealed as described in Example 11, and the third part was melted for 5 minutes at 95° C. and then immediately cooled on ice. Genomic DNA from one individual was also digested with Sau3AI, purified, and reannealed in same manner. Each mixture was then combined with a mixture of perfectly matched PCR fragments prepared as described in Example 1. These fragments were used as a control for migration of perfectly matched DNA. The DNA pool was then analyzed with 2-D gel electrophoresis as described in Example 1. After second dimension gel electrophoresis the gel matrix was placed in UVP GDS-8000 gel documentation system for UV detection of ethidium bromide stained DNA fragments. As shown in FIG. 11a the untreated pooled DNA sample showed the same migration behavior as the perfectly matched control DNA fragments resulting in formation of an arc. Reannealed pooled DNA sample provided similar results as for untreated DNA indicating a high degree of efficiency for the reannealing reaction (FIG. 11b). This is consistent with the markedly reduced complexity of this preparation compared to human genomic DNA. The complex mixture of melted DNA fragments kept on ice showed completely different behavior compared to the perfectly matched control DNA fragments (FIG. 11c) demonstrating inefficient formation of perfectly matched DNA fragments during reannealing. Same was seen for reannealing of total human genome digested with BstY I (FIG. 11d) as expected. This panel of results shows the capability of the methods of invention for evaluation of reannealing efficiency of complex nucleic acids samples.

REFERENCES

1. Crothers, D. M., et al., *DNA bending, flexibility, and helical repeat by cyclization kinetics.* Methods Enzymol, 1992. 212: p. 3-29.
2. Ganguly, A., M. J. Rock; and D. J. Prockop, *Conformation-sensitive gel electrophoresis for rapid detection of single-base differences in double-stranded PCR products and DNA fragments: evidence for solvent-induced bends in DNA heteroduplexes.* Proc Natl Acad Sci USA, 1993. 90(21): p. 10325-9.
3. Ganguly, T., et al., *High throughput fluorescence-based conformation-sensitive gel electrophoresis (F-CSGE) identifies six unique BRCA2 mutations and an overall low incidence of BRCA2 mutations in high-risk BRCA1-negative breast cancer families.* Hum Genet, 1998. 102(5): p. 549-56.
4. Mizuno, T., *Random cloning of bent DNA segments from Escherichia coli chromosome and primary characterization of their structures.* Nucleic Acids Res, 1987. 15(17): p. 6827-41.
5. Anderson, J. N., *Detection, sequence patterns and function of unusual DNA structures.* Nucleic Acids Res, 1986. 14(21): p. 8513-33.
6. Jerkovic, B. and P. H. Bolton, *The curvature of dA tracts is temperature dependent.* Biochemistry, 2000. 39(40): p. 12121-7.
7. Diekmann, S., *Temperature and salt dependence of the gel migration anomaly of curved DNA fragments.* Nucleic Acids Res, 1987. 15(1): p. 247-65.
8. Fangman, B. J. B. a. W. L., *The localization of replication origins on ARS plsmids in S. cerevi.* 1987.
9. Brewer, B. J. and W. L. Fangman, *The localization of replication origins on ARS plasmids in S. cerevisiae.* Cell, 1987. 51(3): p. 463-71.
10. Blackburn, G. M. and M. G. Gait, *Nucleic acids in chemistry and biology.* 2nd ed. 1995, Oxford [England; New York: Oxford University Press. xv, 528.
11. Nightingale, K. P. and K. R. Fox, *Interaction of bleomycin with a bent DNA fragment.* Biochem J, 1992. 284(Pt 3): p. 929-34.
12. Barcelo, F., et al., *Removal of DNA curving by DNA ligands: gel electrophoresis study.* Biochemistry, 1991. 30(20): p. 4863-73.
13. Cons, B. M. and K. R. Fox, *Effects of sequence selective drugs on the gel mobility of a bent DNA fragment.* Biochem Biophys Res Commun, 1990. 171(3): p. 1064-70.
14. Griffith, J., et al., *Visualization of the bent helix in kinetoplast DNA by electron microscopy.* Cell, 1986. 46(5): p. 717-24.

---

The invention claimed is:

1. A method for separating non-circular nucleic acid fragments from a nucleic acid mixture, dependent on their length and conformation, comprising:

providing a mixture of nucleic acid fragments;

loading a sample of said mixture in a gel electrophoresis apparatus and electrophoresing in a first dimension said sample through a polyacrylamide gel matrix under non-denaturing electrophoresis conditions such that said fragments are separated dependent on conformation and length;

electrophoresing said sample in the same gel matrix in a second dimension under a second set of electrophoresis conditions in the presence of a chemical agent and optionally combined with altering a physical agent within the gel matrix which agent/s is/are capable of reducing conformational differences between nucleic acid fragments, such that said fragments are separated in said second dimension dependent on length.

2. The method according to claim 1, wherein the chemical agent is a molecule capable of forming interactions to nucleic acids.

3. The method according to claim 2, wherein the chemical agent is an intercalating molecule.

4. The method according to claim 3, wherein the chemical agent is selected from the group consisting of ethidium bromide, aclacinomycin, chloroquine, distamycin-ellpticine, daunomycin, bleomycin, benzo[a]pyrene, iremycin, proflavin, 5-[(2-Aminoethyl)amino]-2-[2-(diethylamino)ethyl]-2H-[1]benzothiopyrano[4,3,2-cd]-indazol-8-ol trihydrochloride, quiancrine, actinomycin, DEAP fluoranthene, psoralene, bisantrene, ditercalinium, echinomycin, and 1,1'-(4,4,8,8-tetramethyl-4,8-diazaundecamethylene)-bis-4-[-(3-methyl-2,3-dihydro(benzo-1,3-thiazolyl)-2-methylidene] quinolinium tetraiodide.

5. The method according to claim 2, wherein the chemical agent is a groove-binding molecule.

6. The method according to claim 5 wherein the groove-binding molecule is selected from the group consisting of netropsin, distamycin, 2'-(4-hydroxyphenyl)-5-(4-methyl-1-piperazinyl)-2,5'-bi-benzimidazole, and 1-methyl-4-[4-[4-(4-(1-methylquinolinium)amino)benzamido]anilino]pyridinium dichloride.

7. The method according to claim 2, wherein the chemical agent is a charged molecule capable of forming electrostatic interactions to nucleic acids.

8. The method according to claim 1, wherein polymorphic nucleic acids are separated, said nucleic acid sample comprising nucleic acids from one individual or a pool from a plurality of individuals, which nucleic acids have been cleaved, denatured and re-annealed, wherein the denaturing and re-annealing steps are done after mixing of the pooled samples to provide a mixture of homo- and heterohybrids, wherein the method separates mismatched heterohybrids comprising polymorphic nucleic acids from perfectly matched homo- and heterohybrids.

9. The method of claim 8, further comprising the step of isolating the mismatched heterohybrids comprising polymorphic nucleic acids to identify said nucleic acids.

10. The method according to claim 1, wherein a conformational separation of a DNA sample from an individual or pool of individuals is provided, where allele frequency differs between individuals or pools of individuals, comprising a forming a DNA pool by mixing two or more DNA samples together or forming a DNA sample from one individual b annealing specific adaptors to DNA fragments in the pool or DNA sample from one individual, c removing excess adaptors that are not ligated to DNA fragments, d mixing two or more pools together, e denaturing the mixture of pools of DNA samples or DNA sample from an individual, f re-annealing said pools of DNA samples to form DNA duplexes comprising homologous strands, and g separating duplexes containing altered conformation formed either by mismatched base pairs or insertion/deletion loops from perfectly matched DNA duplexes.

11. The method according to any of claims 8-10, wherein separated fragments with normal or unusual conformation are labeled with signals and hybridized to arrayed libraries of selected subsets of genomic clones or metaphase chromosomes.

12. The method of claim 11, wherein the DNA samples are used as material for subtractive hybridization.

13. The method according to claim 11, wherein efficiency of re-annealing of a nucleic acid sample is estimated, wherein the observed relative amount of perfectly matched duplexes provides an indication of efficiency of re-annealing.

14. The method according to claim 1, wherein the chemical agent is a denaturating molecule.

15. The method according to claim 14 wherein the denaturing molecule is selected from the group consisting of aliphatic alcohols; cyclic alcohols; alicyclic compounds; amides; ureas; carbamates; detergents; cyanoguanidine; sulfamide; glycine, and acetonitrile.

16. The method according to claim 1, wherein the nucleic acids fragments are selected from DNA duplexes, RNA duplexes, DNA/RNA duplexes, PNA duplexes, PNA/DNA duplexes, PNA/RNA duplexes, LNA duplexes, LNA/DNA duplexes, and LNA/RNA duplexes.

17. The method according to claim 1, wherein the nucleic acid mixture contains nucleic acid fragments with altered conformation caused by one or more features selected from the group:
- a insertion/deletion loops,
- b mismatched nucleic acids,
- c slipped mispaired nucleic acids,
- d base methylation,
- e base damage,
- f photoproducts resulting from UV damage,
- g base damage by ionizing radiations,
- h oxidative damage of bases,
- i sequences resulting in intrinsic curvature
- j purine-pyrimidine tracts,
- k addition of base adducts,
- l triple stranded nucleic acids,
- m cruciform structures,
- n repetitive sequences,
- o DNA Z-helix,
- p protein bound nucleic acids,
- q hairpin loops,
- r AP sites,
- s base gaps, and
- t nicks.

18. The method according to claim 1, further comprising the step of isolating at least a part of said separated nucleic acid fragments.

19. The method according to claim 1, wherein the nucleic acid sample is derived from a genome from one individual.

20. The method according to claim 19, wherein the sample comprises nucleic acids fragments that have been cleaved, denatured and re-annealed.

21. The method according to claim 1, wherein the sample is a pool comprising a genome from more than one individual.

22. The method according to claim 21, wherein the sample comprises nucleic acids fragments that have been cleaved, denatured and re-annealed, wherein the denaturing and re-annealing steps are done before or after mixing of the samples or pooled samples, to provide a mixture of homo- and heterohybrids.

23. The method according to claim 19 or 21, wherein each sample or pooled sample is a subset of each genome.

24. The method according to claim 23, wherein each sample or pooled sample is a polymorphic subset of each genome.

25. The method according to claim 19 or 21, wherein each sample or pooled sample comprises cDNA derived from each genome.

26. The method according to claim 1, wherein the sample comprises more than one pool of samples.

27. The method according to claim 15, wherein
said aliphatic alcohols are selected from the group consisting of methyl, ethyl, isopropyl, n-propyl, allyl, butyl, isobutyl, and amyl alcohols and ethylene glycol;
said cyclic alcohols are selected from the group consisting of cyclohexyl, benzyl, phenol, and p-methyoxyphenol alcohol and inositol;
said alicyclic compounds are selected from the group consisting of aniline, pyridine, purine, 1,4-dioxane, butyrolactone, and aminotriazole;
said amides are selected from the group consisting of formamide, ethylformamide, dimethylformamide, acetamide, N-ethylacetamide, N,N-dimethylacetamide, propionamide, glycolamide, thioacetamide, valerolactam;
said ureas are selected from the group consisting of carbohydrazide, 1,3-dimethylurea, ethylurea, t-butylurea, thiourea, and allylthiourea;
said carbamates are selected from the group consisting of urethan, N-methylurethan and N-propylurethan; and
said detergents are selected from the group consisting of Tween 40 and Triton X-100.

28. The method according to claim 17, wherein said sequences resulting in intrinsic curvature include adenine tracts and GGCC repeat.

29. A method for separating non-circular nucleic acid fragments from a sample(s) based on their conformation, comprising:
providing a sample of nucleic acid fragments;
loading the sample in a gel electrophoresis apparatus and electrophoresing in a first dimension said sample through a polyacrylamide gel matrix under a first set of pre-determined non-denaturing electrophoresis conditions such that said fragments are separated dependent on conformation and length;
electrophoresing said gel matrix-bound fragments in a second dimension through an agarose matrix under a second set of electrophoresis conditions wherein said fragments are separated dependent on length, such that nucleic acid fragments of equal length but having different conformation are separated.

* * * * *

SEQUENCE LISTING

```
<160> NUMBER OF SEQ ID NOS: 8

<210> SEQ ID NO 1
<211> LENGTH: 241
<212> TYPE: DNA
<213> ORGANISM: Homo sapiens

<400> SEQUENCE: 1
acaacaacaa caacaacaac gacaacaaca acaacaacaa caacaacaac agaagtgtga        60
cccaatttgc actggtgaca atgaaggcag cctttctgg agggttttg gggaaaggtt         120
```

```
tgcactctcc tccctggtat catgggagaa tcccagaaaa agatgggatt tgacacctag      180
aagatgctac tgtggaaagc agggagcaga gaaggaaaga aactcagtcc aagaagacca      240
t                                                                      241

<210> SEQ ID NO 2
<211> LENGTH: 185
<212> TYPE: DNA
<213> ORGANISM: Homo sapiens

<400> SEQUENCE: 2
ggatccttcc ctgatcatag gtaacaactg atgctcactg tacatccctc cccagtcaaa       60
ttcctctcca tgtcctccct tttgatgtgg tgtcaatcac ccccatttgt atttttttacc     120 tttactacat tattattatt attattatta ctactattat tattatttgt gtgcatgtgt     180
gtgag                                                                  185

<210> SEQ ID NO 3
<211> LENGTH: 122
<212> TYPE: DNA
<213> ORGANISM: Homo sapiens

<400> SEQUENCE: 3
gggtgacaaa gcgagactcc atctcaaaaa aagaaaaaaa tgcccaaata gaaactataa       60
gatgttatgg ccttaccttta ctgtcaccac ccatttcccc tgttcatagc aagtttgcct    120
aa                                                                     122

<210> SEQ ID NO 4
<211> LENGTH: 147
<212> TYPE: DNA
<213> ORGANISM: Homo sapiens

<400> SEQUENCE: 4
ggatccacag ccaccactgc cacatccata caaaaacaac acagctccag agtgaacaga       60
gagccgctct ggcttcgatg agacaccaaa taacctcgtg tcccatttc tttattttat      120 tttatttttt attttgattt ttttgcg                                         147

<210> SEQ ID NO 5
<211> LENGTH: 20
<212> TYPE: DNA
<213> ORGANISM: Artificial Sequence
<220> FEATURE:
<223> OTHER INFORMATION: Synthetic reverse primer used for genotyping

<400> SEQUENCE: 5
atggtcttct tggactgagt                                                   20

<210> SEQ ID NO 6
<211> LENGTH: 22
<212> TYPE: DNA
<213> ORGANISM: Artificial Sequence
<220> FEATURE:
<223> OTHER INFORMATION: Synthetic reverse primer used for genotyping

<400> SEQUENCE: 6
cagtcaaatt cctctccatg tc                                                22

<210> SEQ ID NO 7
<211> LENGTH: 20
<212> TYPE: DNA
<213> ORGANISM: Artificial Sequence
```

```
-continued

<220> FEATURE:
<223> OTHER INFORMATION: Synthetic reverse primer used for genotyping

<400> SEQUENCE: 7
ggcaaacttg ctatgaacag                                                    20

<210> SEQ ID NO 8
<211> LENGTH: 19
<212> TYPE: DNA
<213> ORGANISM: Artificial Sequence
<220> FEATURE:
<223> OTHER INFORMATION: Synthetic reverse primer used for genotyping

<400> SEQUENCE: 8
accactgcca catccatac                                                     19
```